United States Patent
Reglos et al.

(10) Patent No.: US 8,740,948 B2
(45) Date of Patent: Jun. 3, 2014

(54) SPINAL SPACER FOR CERVICAL AND OTHER VERTEBRA, AND ASSOCIATED SYSTEMS AND METHODS

(75) Inventors: Joey C. Reglos, Lake Forest, CA (US); Moti Altarac, Irvine, CA (US)

(73) Assignee: VertiFlex, Inc., San Clemente, CA (US)

( * ) Notice: Subject to any disclaimer, the term of this patent is extended or adjusted under 35 U.S.C. 154(b) by 307 days.

(21) Appl. No.: 12/969,328

(22) Filed: Dec. 15, 2010

(65) Prior Publication Data
US 2011/0313457 A1 Dec. 22, 2011

Related U.S. Application Data

(60) Provisional application No. 61/286,523, filed on Dec. 15, 2009.

(51) Int. Cl.
*A61B 17/88* (2006.01)
*A61B 17/70* (2006.01)

(52) U.S. Cl.
CPC ............. *A61B 17/7065* (2013.01); *A61B 17/88* (2013.01)
USPC .......................................... 606/279; 606/249

(58) Field of Classification Search
CPC .................................................... A61B 17/7068
USPC ........................................ 606/246, 248, 249
See application file for complete search history.

(56) References Cited

U.S. PATENT DOCUMENTS

| | | |
|---|---|---|
| 2,248,054 A | 7/1941 | Becker |
| 2,677,369 A | 5/1954 | Knowles |
| 3,242,120 A | 3/1966 | Steuber |
| 3,648,691 A | 3/1972 | Lumb et al. |
| 3,986,383 A | 10/1976 | Petteys |
| 4,632,101 A | 12/1986 | Freedland |
| 4,685,447 A | 8/1987 | Iversen et al. |
| 4,895,564 A | 1/1990 | Farrell |
| 5,011,484 A | 4/1991 | Breard et al. |

(Continued)

FOREIGN PATENT DOCUMENTS

| | | |
|---|---|---|
| DE | 69507480 | 9/1999 |
| EP | 322334 | 6/1989 |

(Continued)

OTHER PUBLICATIONS

European Office Action Application No. EP05849654.8; Applicant: The Board of Trustees of the Leland Stanford Junior University; Date of Completion: Jun. 21, 2011, 4 pages.

(Continued)

*Primary Examiner* — Ellen C Hammond
(74) *Attorney, Agent, or Firm* — Perkins Coie LLP

(57) ABSTRACT

Spinal spacers for cervical and other vertebra, and associated systems and methods are disclosed. A device in accordance with a particular embodiment includes a hook member having a hook positioned to extend in a first direction, a post carried by the hook member and extending axially in a second direction transverse to the first direction, and a cam surface carried by the hook member. An actuator device is movably engaged with the post, and a spinal spacer is pivotably coupled to one of the actuator device and the post. The spinal spacer is axially movable relative to the hook member and has a spacing element in contact with the cam surface to pivot outwardly away from the post as the actuator device moves.

16 Claims, 22 Drawing Sheets

(56) References Cited

U.S. PATENT DOCUMENTS

| | | |
|---|---|---|
| 5,015,247 A | 5/1991 | Michelson |
| 5,019,081 A | 5/1991 | Watanabe |
| 5,059,193 A | 10/1991 | Kuslich |
| 5,092,866 A | 3/1992 | Breard et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura |
| 5,904,636 A | 5/1999 | Chen et al. |
| 5,904,686 A | 5/1999 | Zucherman et al. |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zuckerman et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,319 B2 | 6/2003 | Goble et al. |
| 6,582,433 B2 | 6/2003 | Yun |
| 6,582,451 B1 | 6/2003 | Marucci et al. |
| 6,610,065 B1 | 8/2003 | Branch et al. |
| 6,610,091 B1 | 8/2003 | Reiley |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,716,245 B2 | 4/2004 | Pasquet et al. |
| 6,733,534 B2 | 5/2004 | Sherman |
| 6,746,485 B1 | 6/2004 | Zucherman et al. |
| 6,761,720 B1 | 7/2004 | Senegas et al. |
| 6,769,983 B2 | 8/2004 | Slomiany |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,835,205 B2 | 12/2004 | Atkinson et al. |
| 6,858,029 B2 | 2/2005 | Yeh et al. |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |

(56) References Cited

U.S. PATENT DOCUMENTS

| | | | |
|---|---|---|---|
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| 7,727,233 B2 | 6/2010 | Blackwell et al. |
| 7,742,795 B2 | 6/2010 | Stone et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,688 B2 | 11/2010 | Boyer, II et al. |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 2001/0031965 A1 | 10/2001 | Zucherman et al. |
| 2002/0143331 A1 | 10/2002 | Zucherman et al. |
| 2003/0040746 A1 | 2/2003 | Mitchell et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2004/0087947 A1 | 5/2004 | Lim et al. |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1* | 11/2006 | Zucherman et al. ............ 606/61 |
| 2006/0265066 A1 | 11/2006 | Zucherman et al. |
| 2006/0265067 A1 | 11/2006 | Zucherman et al. |
| 2006/0271044 A1* | 11/2006 | Petrini et al. .................... 606/61 |

(56) References Cited

U.S. PATENT DOCUMENTS

| | | |
|---|---|---|
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071378 A1 | 3/2008 | Zucherman et al. |
| 2008/0086212 A1 | 4/2008 | Zucherman et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0183210 A1 | 7/2008 | Zucherman et al. |
| 2008/0188895 A1 | 8/2008 | Cragg et al. |
| 2008/0195152 A1* | 8/2008 | Altarac et al. .............. 606/249 |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234824 A1 | 9/2008 | Youssef et al. |
| 2008/0287997 A1 | 11/2008 | Altarac et al. |
| 2008/0288075 A1 | 11/2008 | Zucherman et al. |
| 2008/0294263 A1* | 11/2008 | Altarac et al. ............ 623/17.16 |
| 2008/0319550 A1 | 12/2008 | Altarac et al. |
| 2009/0118833 A1 | 5/2009 | Hudgins et al. |
| 2009/0125030 A1 | 5/2009 | Tebbe et al. |
| 2009/0138046 A1 | 5/2009 | Altarac et al. |
| 2009/0138055 A1 | 5/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0262243 A1 | 10/2010 | Zucherman et al. |
| 2010/0305611 A1 | 12/2010 | Zucherman et al. |

FOREIGN PATENT DOCUMENTS

| | | |
|---|---|---|
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |

(56) References Cited

FOREIGN PATENT DOCUMENTS

| | | | |
|---|---|---|---|
| EP | 1343424 | B1 | 9/2004 |
| EP | 1454589 | A1 | 9/2004 |
| EP | 1148850 | B1 | 4/2005 |
| EP | 1299042 | B1 | 3/2006 |
| EP | 1578314 | B1 | 5/2007 |
| EP | 1675535 | B1 | 5/2007 |
| WO | WO-9404088 | A1 | 3/1994 |
| WO | WO-9426192 | A1 | 11/1994 |
| WO | WO-9525485 | A1 | 9/1995 |
| WO | WO-9531158 | A1 | 11/1995 |
| WO | WO-9600049 | A1 | 1/1996 |
| WO | WO-9829047 | A1 | 7/1998 |
| WO | WO-9921500 | A1 | 5/1999 |
| WO | WO-9921501 | A1 | 5/1999 |
| WO | WO-9942051 | A1 | 8/1999 |
| WO | WO-0013619 | A1 | 3/2000 |
| WO | WO-0044319 | A1 | 8/2000 |
| WO | WO-0044321 | A2 | 8/2000 |
| WO | WO-0128442 | A1 | 4/2001 |
| WO | WO-0191657 | A1 | 12/2001 |
| WO | WO-0191658 | A1 | 12/2001 |
| WO | WO-0203882 | A2 | 1/2002 |
| WO | WO-0207623 | A1 | 1/2002 |
| WO | WO-0207624 | A1 | 1/2002 |
| WO | WO-02051326 | A1 | 7/2002 |
| WO | WO-02067793 | A2 | 9/2002 |
| WO | WO-02071960 | A1 | 9/2002 |
| WO | WO-02076336 | A2 | 10/2002 |
| WO | WO 03007791 | A2 | 1/2003 |
| WO | WO-03007829 | A1 | 1/2003 |
| WO | WO-03008016 | A2 | 1/2003 |
| WO | WO-03015646 | A2 | 2/2003 |
| WO | WO-03024298 | A2 | 3/2003 |
| WO | WO-03045262 | A2 | 6/2003 |
| WO | WO-03099147 | A1 | 12/2003 |
| WO | WO-03101350 | A1 | 12/2003 |
| WO | WO-2004073533 | A1 | 9/2004 |
| WO | WO-2004110300 | A2 | 12/2004 |
| WO | WO-2005009300 | A1 | 2/2005 |
| WO | WO-2005013839 | A2 | 2/2005 |
| WO | WO-2005025461 | A2 | 3/2005 |
| WO | WO-2005041799 | A1 | 5/2005 |
| WO | WO-2005044152 | A1 | 5/2005 |
| WO | WO-2005055868 | A2 | 6/2005 |
| WO | WO-2005079672 | A2 | 9/2005 |
| WO | WO-2005115261 | A1 | 12/2005 |
| WO | WO-2006033659 | A2 | 3/2006 |
| WO | WO-2006034423 | A2 | 3/2006 |
| WO | WO-2006039243 | | 4/2006 |
| WO | WO-2006039260 | A2 | 4/2006 |
| WO | WO-2006045094 | A2 | 4/2006 |
| WO | WO-2006063047 | A2 | 6/2006 |
| WO | WO-2006065774 | A1 | 6/2006 |
| WO | WO-2006102269 | A2 | 9/2006 |
| WO | WO-2006102428 | A1 | 9/2006 |
| WO | WO-2006102485 | A2 | 9/2006 |
| WO | WO-2006107539 | A1 | 10/2006 |
| WO | WO-2006110462 | A2 | 10/2006 |
| WO | WO-2006110464 | A1 | 10/2006 |
| WO | WO-2006110767 | A1 | 10/2006 |
| WO | WO-2006113080 | A2 | 10/2006 |
| WO | WO-2006113406 | A2 | 10/2006 |
| WO | WO-2006113814 | A2 | 10/2006 |
| WO | WO-2006118945 | A1 | 11/2006 |
| WO | WO-2006119235 | A1 | 11/2006 |
| WO | WO-2006119236 | A2 | 11/2006 |
| WO | WO-2006135511 | A1 | 12/2006 |
| WO | WO-2007015028 | A1 | 2/2007 |
| WO | WO-2007035120 | A1 | 3/2007 |
| WO | WO-2007075375 | A2 | 7/2007 |
| WO | WO-2007075788 | A2 | 7/2007 |
| WO | WO-2007075791 | A2 | 7/2007 |
| WO | WO-2007089605 | A2 | 8/2007 |
| WO | WO-2007089905 | A2 | 8/2007 |
| WO | WO-2007089975 | A1 | 8/2007 |
| WO | WO-2007097735 | A2 | 8/2007 |
| WO | WO-2007109402 | A2 | 9/2007 |
| WO | WO-2007110604 | A1 | 10/2007 |
| WO | WO-2007111795 | A1 | 10/2007 |
| WO | WO-2007111979 | A2 | 10/2007 |
| WO | WO-2007111999 | A2 | 10/2007 |
| WO | WO-2007117882 | A1 | 10/2007 |
| WO | WO-2007121070 | A2 | 10/2007 |
| WO | WO-2007127550 | A2 | 11/2007 |
| WO | WO-2007127588 | A1 | 11/2007 |
| WO | WO-2007127677 | A1 | 11/2007 |
| WO | WO-2007127689 | A2 | 11/2007 |
| WO | WO-2007127694 | A2 | 11/2007 |
| WO | WO-2007127734 | A2 | 11/2007 |
| WO | WO-2007127736 | A2 | 11/2007 |
| WO | WO-2007131165 | A2 | 11/2007 |
| WO | WO-2007134113 | A2 | 11/2007 |
| WO | WO-2008048645 | A2 | 4/2008 |

OTHER PUBLICATIONS

Non-Final Office Action; U.S. Appl. No. 12/205,511 Mailing Date: Apr. 20, 2011 9 pages.
Non-Final Office Action; U.S. Appl. No. 12/358,010 Mailing Date: Jul. 14, 2011; 9 pages.
Supplementary European Search Report; Application No. EP07861426.0; Applicant: Vertiflex, Inc; Date of Completion: Jun. 7, 2011, 6 pages.
Supplementary European Search Report; Application No. EP11151901.3; Applicant: Vertiflex, Inc; Date of Completion: Apr. 7, 2011, 6 pages.
Final Office Action; U.S. Appl. No. 10/970,843; Mailing Date: Feb. 12, 2009, 7 pages.
Final Office Action; U.S. Appl. No. 10/970,843; Mailing Date: Jul. 2, 2010, 9 pages.
Final Office Action; U.S. Appl. No. 11/006,502; Mailing Date: Aug. 17, 2009, 7 pages.
Final Office Action; U.S. Appl. No. 11/006,521; Mailing Date: May 17, 2010, 10 pages.
Final Office Action; U.S. Appl. No. 11/006,521; Mailing Date: Dec. 5, 2008, 10 pages.
Final Office Action; U.S. Appl. No. 11/052,002; Mailing Date: Apr. 1, 2009, 7 pages.
Final Office Action; U.S. Appl. No. 11/052,002; Mailing Date: Sep. 1, 2010, 7 pages.
Final Office Action; U.S. Appl. No. 11/079,006; Mailing Date: Nov. 10, 2009, 7 pages.
Final Office Action; U.S. Appl. No. 11/190,496; Mailing Date: May 19, 2009, 8 pages.
Final Office Action; U.S. Appl. No. 11/305,820; Mailing Date: Jun. 16, 2008, 9 pages.
Final Office Action; U.S. Appl. No. 11/314,712; Mailing Date: Sep. 4, 2009, 9 pages.
Final Office Action; U.S. Appl. No. 11/582,874; Mailing Date: Sep. 10, 2010, 10 pages.
International Search Report and Written Opinion; Application No. PCT/US2005/038026; Mailing Date: Apr. 22, 2008, 9 pages.
International Search Report and Written Opinion; Application No. PCT/US2005/044256; Mailing Date: Jul. 28, 2006, 7 pages.
International Search Report and Written Opinion; Application No. PCT/US2006/047824; Mailing Date: Oct. 16, 2008, 3 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 13 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/008382; Mailing Date: Mar. 2, 2009, 12 pages.

(56) References Cited

OTHER PUBLICATIONS

International Search Report and Written Opinion; Application No. PCT/US2008/008983; Mailing Date: Feb. 23, 2009, 7 pages.
International Search Report and Written Opinion; Application No. PCT/US2008/075487; Mailing Date: Dec. 31, 2008, 7 pages.
International Search Report and Written Opinion; Application No. PCT/US2008/087527; Mailing Date: Jul. 30, 2009, 7 pages.
International Search Report and Written Opinion; Application No. PCT/US2009/031150; Mailing Date: Aug. 28, 2009, 5 pages.
International Search Report and Written Opinion; Application No. PCT/US2009/031710; Mailing Date: Sep. 1, 2009, 10 pages.
International Search Report and Written Opinion; Application No. PCT/US2009/036561; Mailing Date: Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Non-Final Office Action; U.S. Appl. No. 10/970,843; Mailing Date: Aug. 29, 2008, 9 pages.
Non-Final Office Action; U.S. Appl. No. 10/970,843; Mailing Date: Oct. 8, 2009, 8 pages.
Non-Final Office Action; U.S. Appl. No. 11/006,502; Mailing Date: Nov. 7, 2008, 7 pages.
Non-Final Office Action; U.S. Appl. No. 11/006,521; Mailing Date: Feb. 28, 2008, 13 pages.
Non-Final Office Action; U.S. Appl. No. 11/006,521; Mailing Date: Aug. 26, 2009, 9 pages.
Non-Final Office Action; U.S. Appl. No. 11/052,002; Mailing Date: Sep. 18, 2007, 7 pages.
Non-Final Office Action; U.S. Appl. No. 11/052,002; Mailing Date: Dec. 24, 2009, 6 pages.
Non-Final Office Action; U.S. Appl. No. 11/079,006; Mailing Date: Jan. 30, 2009, 7 pages.
Non-Final Office Action; U.S. Appl. No. 11/079,006; Mailing Date: Sep. 18, 2007, 6 pages.
Non-Final Office Action; U.S. Appl. No. 11/190,496; Mailing Date: Aug. 25, 2008, 6 pages.
Non-Final Office Action; U.S. Appl. No. 11/190,496; Mailing Date: Oct. 31, 2007, 7 pages.
Non-Final Office Action; U.S. Appl. No. 11/305,820; Mailing Date: Oct. 9, 2007, 8 pages.
Non-Final Office Action; U.S. Appl. No. 11/314,712; Mailing Date: Jan. 21, 2009, 8 pages.
Non-Final Office Action; U.S. Appl. No. 11/582,874; Mailing Date: Jan. 4, 2010, 9 pages.
Non-Final Office Action; U.S. Appl. No. 11/593,995; Mailing Date: Apr. 19, 2010, 10 pages.
Non-Final Office Action; U.S. Appl. No. 12/338,793; Mailing Date: Sep. 21, 2010, 9 pages.
Supplementary European Search Report; Application No. EP05849654.8; Applicant: Vertiflex, Inc; Date of Completion: May 15, 2009, 10 pages.
Supplementary European Search Report; Application No. EP07861721.4; Applicant: Vertiflex, Inc; Date of Completion: Nov. 24, 2009, 6 pages.
Supplementary European Search Report; Application No. EP09170304.1; Applicant: Vertiflex, Inc; Date of Completion: Nov. 11, 2009, 5 pages.
Supplementary European Search Report; Application No. EP09170338.9; Applicant: Vertiflex, Inc; Date of Completion: Nov. 12, 2009, 6 pages.
Swan, Colby, "Preliminary Design and Experimental Studies of a Novel Soft Implant for Correcting Sogittal P{lane Instability in the Lumbar Spine," Spine, 1997, 22(16), 1826-1827.

* cited by examiner

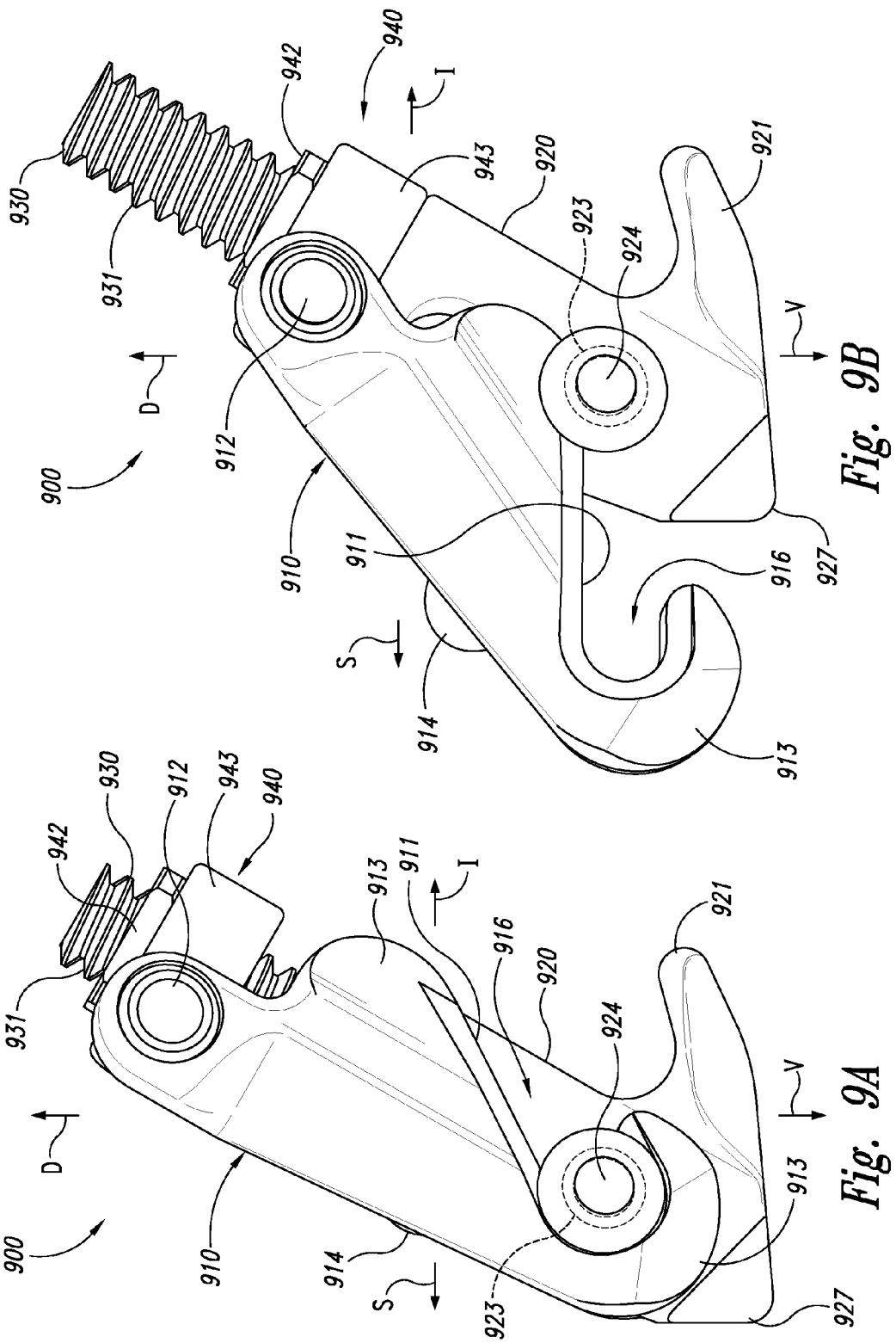

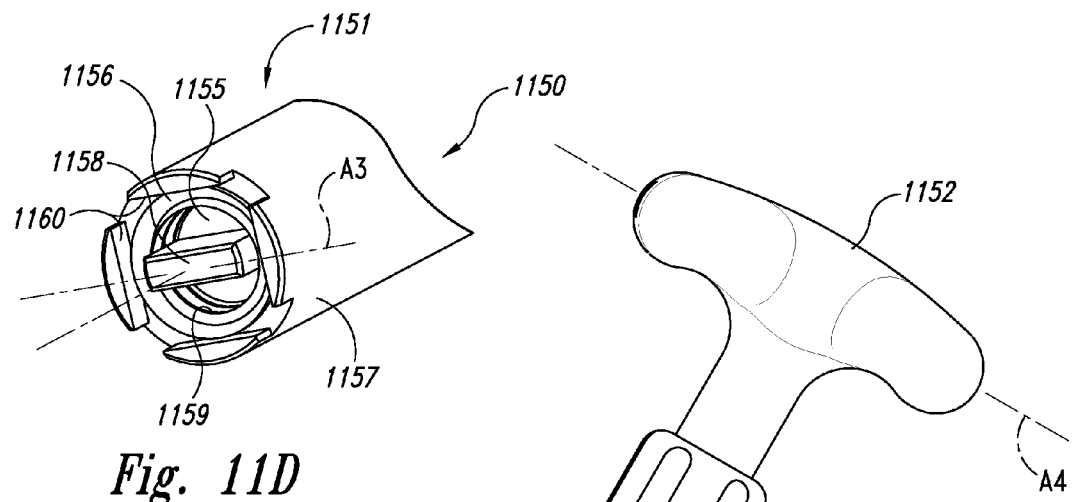
*Fig. 11D*
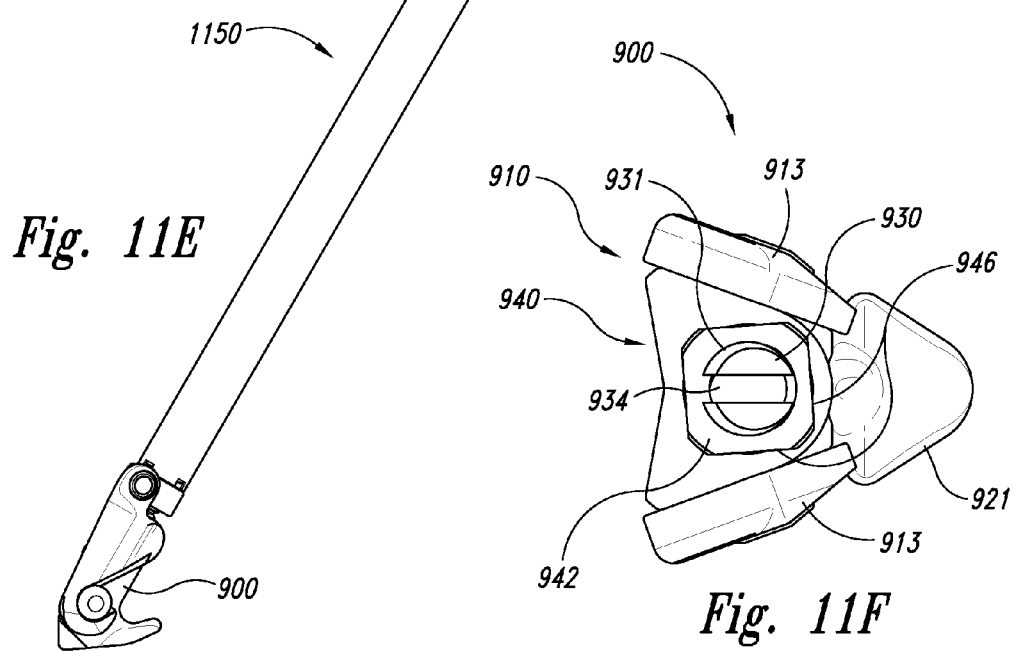
*Fig. 11E*
*Fig. 11F*

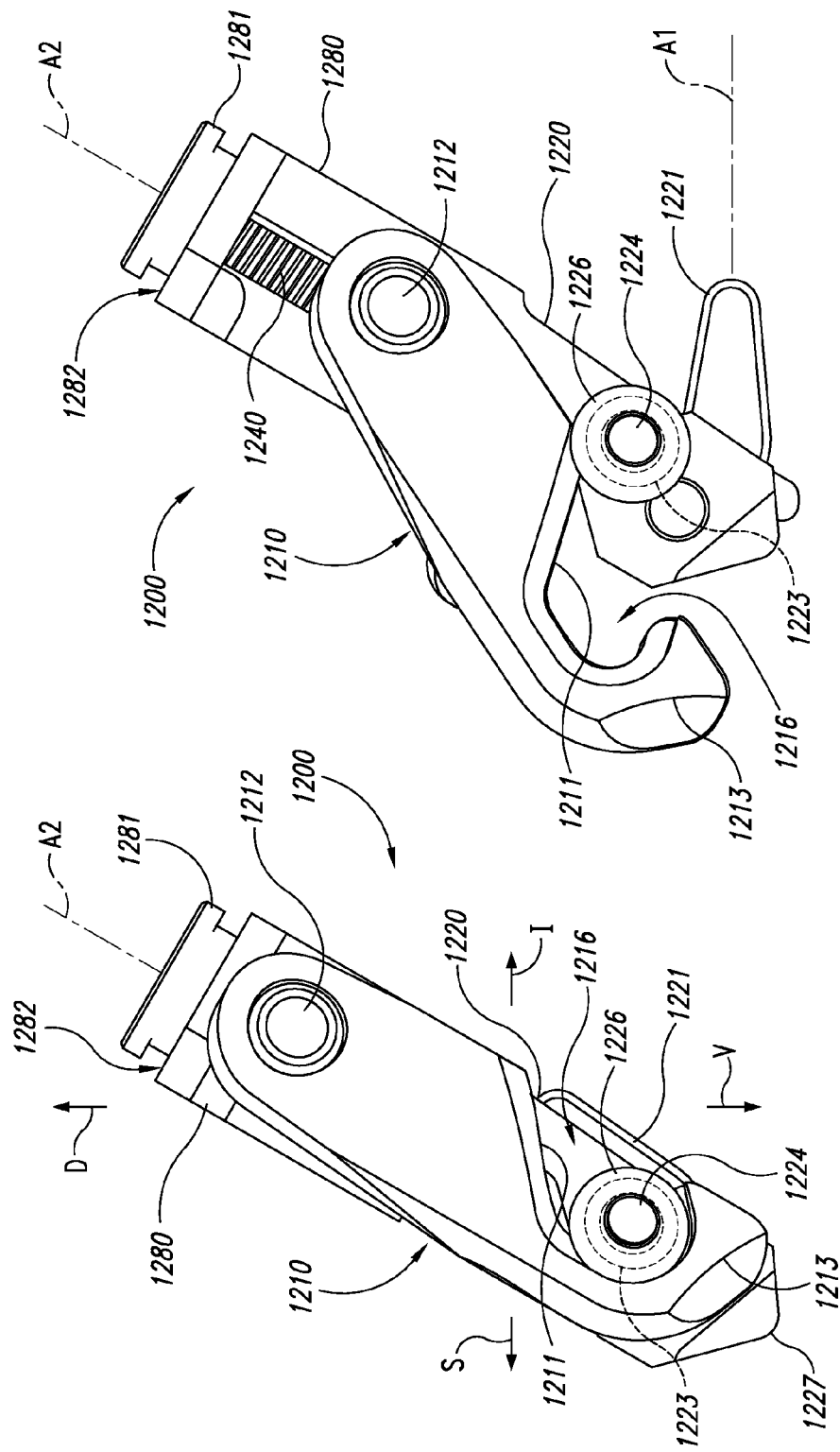

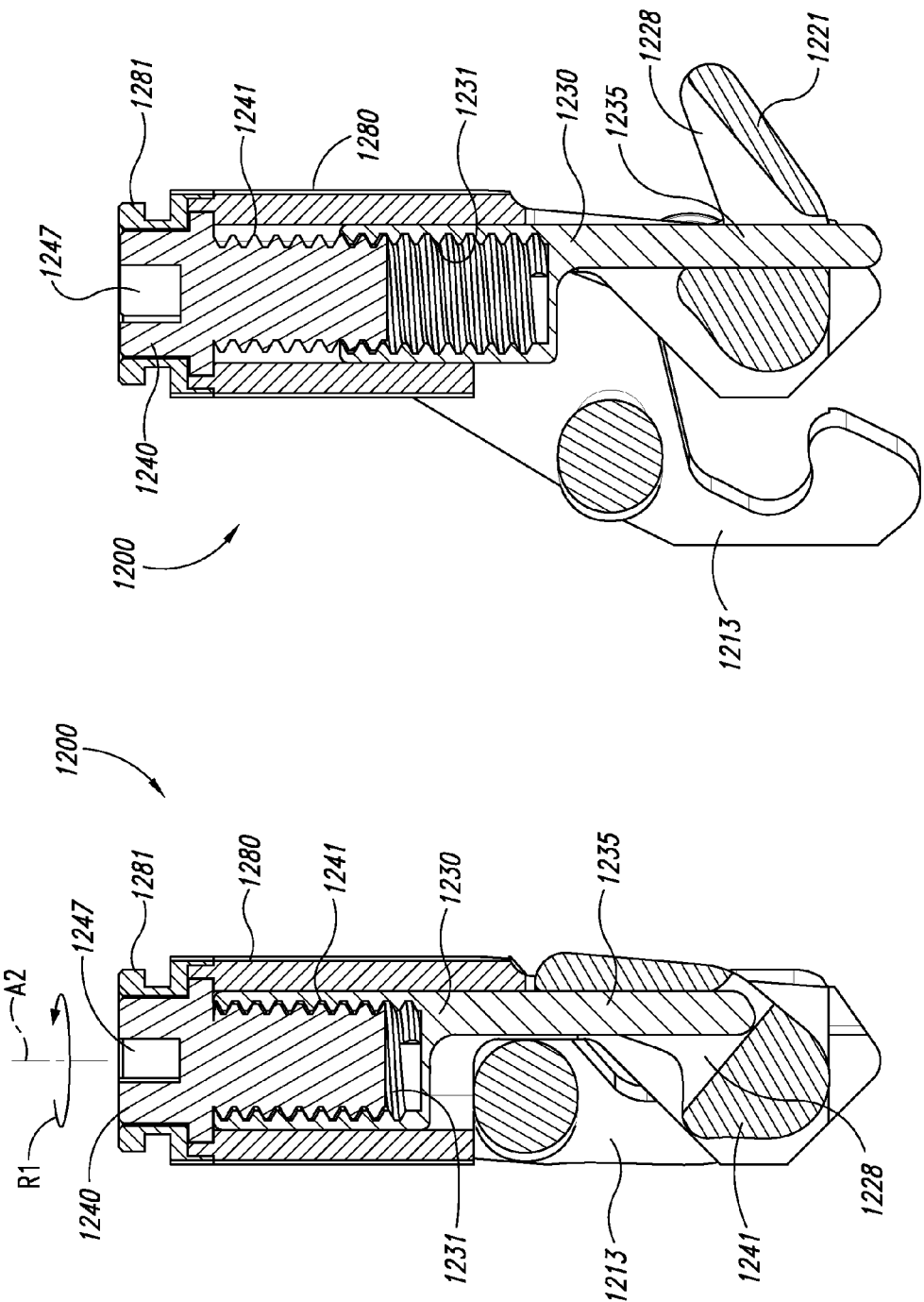

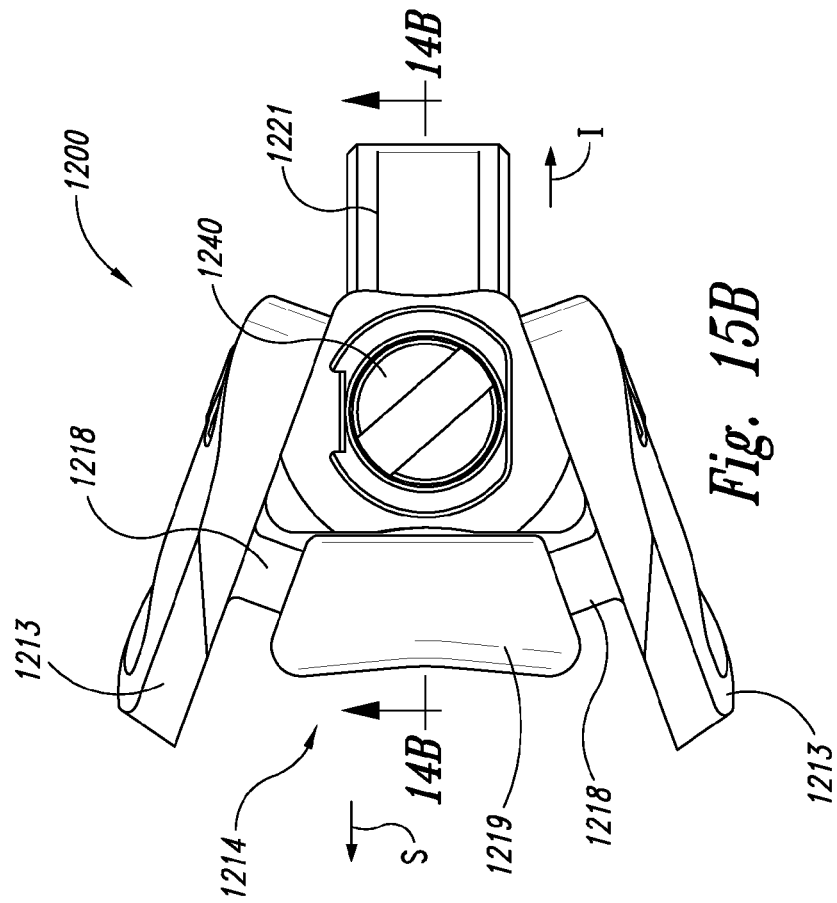
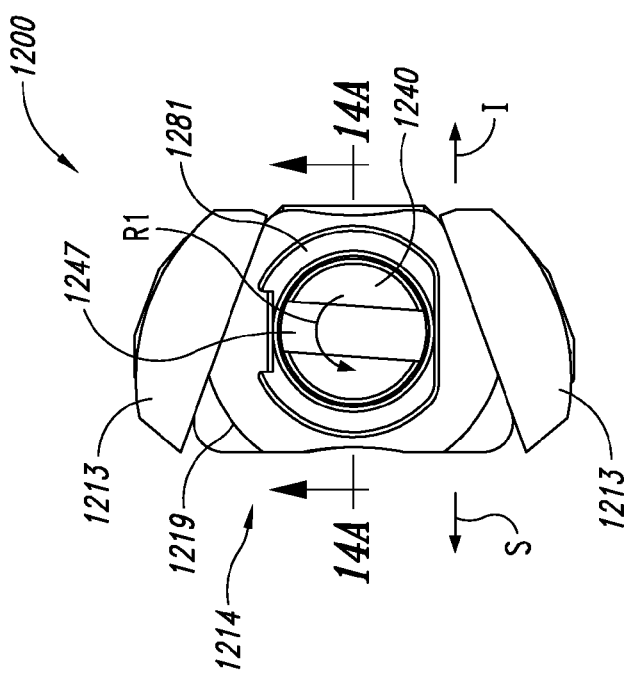
Fig. 15B
Fig. 15A

SPINAL SPACER FOR CERVICAL AND OTHER VERTEBRA, AND ASSOCIATED SYSTEMS AND METHODS

CROSS-REFERENCE TO RELATED APPLICATIONS

This application claims priority to and the benefit of U.S. Provisional Patent Application No. 61/286,523, filed Dec. 15, 2009 and titled SPINAL SPACER FOR CERVICAL AND OTHER VERTEBRA, AND ASSOCIATED SYSTEMS AND METHODS, the disclosure of which is incorporated herein by reference in its entirety.

TECHNICAL FIELD

The present disclosure is directed to spinal spacers for cervical and other vertebra, and associated systems and methods.

BACKGROUND

Spinal pain has long been a source of patient discomfort and a limitation on the patient's mobility and quality of life. Spine fusion (arthrodesis) is a procedure in which two or more adjacent vertebral bodies are fused together. It is one of the most common approaches for alleviating various types of spinal pain, particularly pain associated with one or more affected intervertebral discs. While spine fusion generally helps to eliminate certain types of pain, it has been shown to decrease function by limiting the range of motion for patients in flexion, extension, rotation, and lateral bending. Furthermore, the fusion creates increased stresses on adjacent non-fused vertebra, and accelerated degeneration of the vertebra. Additionally, pseudarthrosis (resulting from an incomplete or ineffective fusion) may not provide the expected pain relief for the patient. Also, the device(s) used for fusion, whether artificial or biological, may migrate out of the fusion site, creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

More recently, surgical-based technologies, referred to as "dynamic posterior stabilization," have been developed to address spinal pain resulting from one or more disorders, particularly when more than one structure of the spine has been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247; 5,484,437; 5,489,308; 5,609,636; 5,658,337; 5,741,253; 6,080,155; 6,096,038; 6,264,656; and 6,270,498. These types of systems typically involve the use of screws that are positioned in the vertebral body through the pedicle. Because these types of systems require the use of pedicle screws, implanting the systems is often more invasive than implanting interspinous spacers.

Examples of interspinous spacers are disclosed in U.S. Pat. Nos. Re 36,211; 5,645,599; 6,149,642; 6,500,178; 6,695,842; 6,716,245; and 6,761,720. The spacers, which are made of either a hard or a compliant material, are placed between the adjacent spinous processes of adjacent vertebra. While slightly less invasive than the procedures required for implanting a pedicle screw-based dynamic stabilization system, hard or solid interspinous spacers still require that the muscle tissue and the supraspinous and interspinous ligaments be dissected. Accordingly, in some instances, compliant interspinous spacers are preferred. However, the compliancy of such spacers makes them more susceptible to displacement or migration over time. One type of spacer developed by the assignee of the present application, and disclosed in U.S. patent application Ser. No. 11/314,712, is directed to rigid interspinous spacers that may be deployed from a posterior direction so as to reduce the amount of tissue dissected during implantation. These spacers also include deployable features that are stowed as the spacer is implanted to provide a low profile shape, and are then expanded once the spacer is implanted to provide the structure that stabilizes neighboring vertebra. Such devices have proven beneficial in many instances. However, there remains a need for reducing the invasiveness of an interspinous implant, while at the same time (a) reducing the likelihood for the implant to migrate, and (b) maintaining or improving the ability of the implant to provide suitable stability.

SUMMARY

The following summary is provided for the benefit of the reader only, and is not intended to limit in any way the invention as set forth by the claims. Aspects of the present disclosure are directed generally to spinal spacers for cervical and other vertebra, and associated systems and methods. A device for stabilizing a first vertebra relative to a second vertebra in accordance with a particular embodiment includes a hook member having a hook positioned to extend in a first direction, and a post carried by the hook member and extending axially in a second direction transverse to the first direction. The device can further include a cam surface carried by the hook member, and an actuator device moveably engaged with the post. The device can still further include a spinal spacer pivotably coupled to one of the actuator device and the post, and axially moveable relative to the hook member. The spinal spacer can have a spacing element in contact with the cam surface to pivot outwardly away from the post as the actuator device moves.

In further particular embodiments, the device can include one or more of several additional features, For example, the post can have internal threads and the actuator device can have external threads threadably engaged with the internal threads. In another embodiment, this arrangement can be reversed with the post having external threads and the actuator device having internal threads. The hook member can include a first portion and a second portion movably coupled to the first portion. At least one of the first and second portions is movable relative to the other between a stowed position and a deployed position, with the second portion extending in the first direction when in the deployed position. In another embodiment, the cam surface can be a first cam surface, and the device can further comprise a second cam surface carried by the hook member. The spacing element can be a first spacing element, and the spinal spacer can include a second spacing element in contact with the second cam surface to pivot outwardly away from the post as the actuator device moves axially. The first and second spacing elements can be pivotable relative to the post about a common axis, or about different axes.

Other embodiments of the disclosure are directed to methods for stabilizing a first vertebra relative to a second vertebra. A method in accordance with one embodiment includes inserting a hook member into an interspinous space between a first vertebra and a second, neighboring vertebra, with the hook member contacting the first vertebra, and with a post carried by the host member extending axially from the hook member. The method can further include moving an actuator relative to the post to pivot a spinal spacer outwardly away from the post and into contact with the second vertebra. The method can still further include continuing to move the actuator axially along the post while the hook member contacts the first vertebra and the spinal spacer contacts the second vertebra to force the first and second vertebra apart from each other.

In particular embodiments, the hook member can be inserted between the C3 and C4 cervical vertebra. The hook member can be inserted so as to project in an inferior direction, and can be inserted from a posterior position. In further particular embodiments, the spinal spacer can include spacing elements having spaced apart portions that are positioned laterally on opposite sides of the second vertebra to at least restrict lateral motion of the device relative to the first and second vertebra. The hook member can extend into a vertebral foramen of the first vertebra to at least restrict dorsal motion of the device.

BRIEF DESCRIPTION OF THE DRAWINGS

FIGS. 9A and 9B illustrate a device configured in accordance with still another embodiment of the disclosure, in a stowed configuration (FIG. 9A) and a deployed configuration (FIG. 9B).

FIG. 11D is a bottom isometric view of the distal end of the actuator tool shown in FIGS. 11A-11C.

FIG. 11E is a side view of the actuator tool shown in FIGS. 11A-11D, engaged with the device shown in FIGS. 9A-10B, in accordance with an embodiment of the disclosure.

FIG. 11F is a top view of the device shown in FIGS. 9A and 9B, and is generally similar to FIG. 10A.

FIGS. 12A-12B are partially schematic, side view illustrations of a device configured in accordance with yet another embodiment of the disclosure, shown in a stowed configuration (FIG. 12A) and a deployed configuration (FIG. 12B).

FIGS. 14A and 14B illustrate cross-sectional views of the device shown in FIGS. 12A-13B in a stowed configuration (FIG. 14A) and deployed configuration (FIG. 14B).

FIGS. 15A and 15B are top views of the device shown in FIGS. 14A and 14B, in the stowed configuration (FIG. 15A) and deployed configuration (FIG. 15B).

DETAILED DESCRIPTION

A. Overview

Several embodiments of intervertebral spacers, systems, and associated methods are described below. The term "intervertebral" generally refers to the positional relationship between two neighboring vertebral bodies of a human spine. A person skilled in the relevant art will also understand that the devices, systems, and/or methods disclosed herein may have additional embodiments, and that embodiments of the devices, systems, and methods disclosed herein may not include all the details of the embodiments described below with reference to FIGS. 1A-17H.

For purposes of organization, the following discussion is divided into several sections, each generally associated with one of four particular embodiments of spinal spacer devices, or tools used to implant and/or deploy such devices. While the following discussion is divided to enhance the reader's understanding of each embodiment, it will be understood that aspects of each embodiment may be combined with other embodiments without departing from the scope of the present disclosure.

B. Spinal Spacer Device in Accordance with a First Embodiment

Figure 1A:
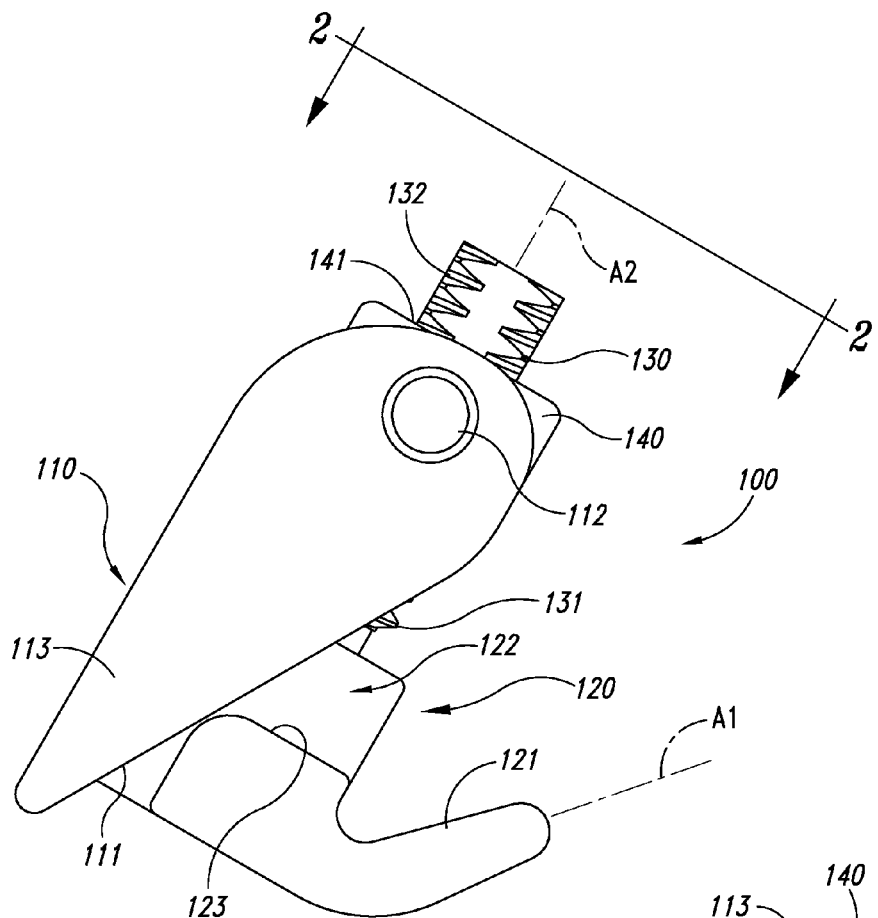
FIG. 1A is a partially schematic side view of an interspinous spacer device configured in accordance with an embodiment of the disclosure.
Figure 1B:
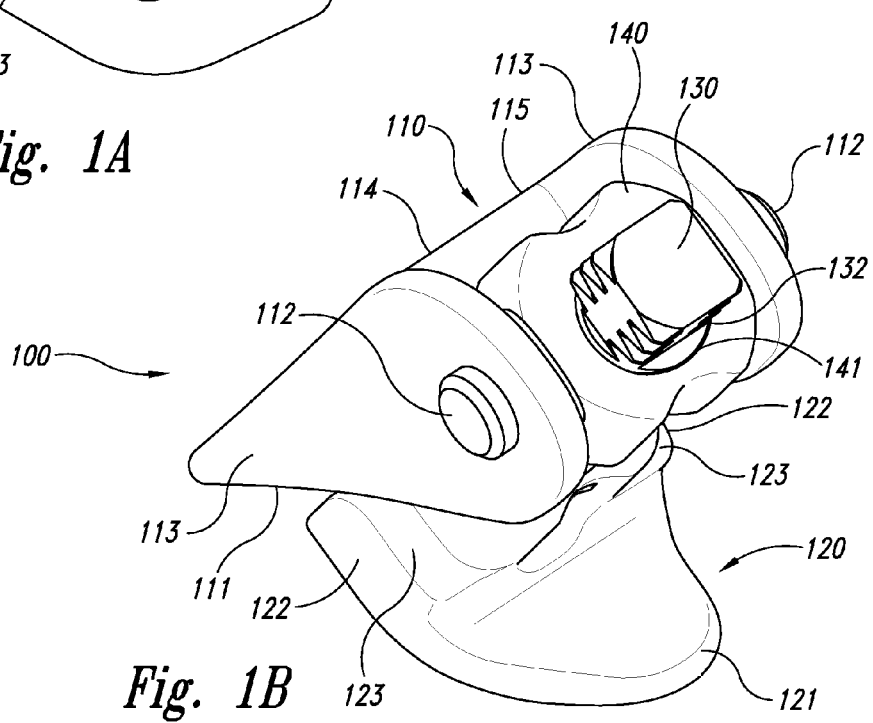
FIG. 1B is a top isometric view of the device shown in FIG. 1A.

FIG. 1A is a partially schematic side view of a spinal spacer device 100 configured in accordance with a first embodiment of the disclosure. FIG. 1B is a top isometric view of the device 100 shown in FIG. 1A. Referring to FIGS. 1A and 1B together, the device 100 includes a hook member 120 having a hook 121 that projects along a first axis A1. The hook member 120 carries a post 130 that extends along a second axis A2, transverse to the first axis A1. The hook 121 is configured and positioned to fit within the vertebral foramen of a patient's vertebra. The device 100 further includes a spinal spacer 110 that moves between a stowed position, shown in FIGS. 1A and 1B, and a deployed position described further below with reference to FIGS. 1C and 3. An actuator device 140 moves the spinal spacer 110 from the stowed position to the deployed position.

In a particular embodiment, the spinal spacer 110 is pivotably attached to the actuator device 140 via a pair of pivot pins 112. The actuator device 140 includes internal actuator threads 141 that are engaged with corresponding external post threads 131 of the post 130. As the post 130 is rotated about the second axis A2, the actuator device 140 travels axially along the post 130. The post 130 includes a tool grip portion 132 that allows a tool to grip and rotate the post 130.

The spinal spacer 110 includes a pair of spacing elements 113, each with a corresponding spacer surface 111. The spacer surfaces 111 bear against corresponding cam surfaces 123 carried by the hook member 120. For example, the hook member 120 can include oppositely facing sides 122, each having a corresponding cam surface 123 against which the corresponding spacer surface 111 bears. As the actuator device 140 moves downwardly along the post 130, each spacer surface 111 slides against the corresponding cam surface 123, and the spinal spacer 110 pivots outwardly.

Referring now to FIG. 1B, each of the spacing elements 113 can have a wing-type shape, in a particular embodiment. The spacing elements 113 are held in a fixed position relative to each other by a saddle 114. The saddle 114 and the spacing elements 113 include vertebral contact surfaces 115 that press against a superior vertebra when deployed. In the illustrated embodiment, the pivot pins 112 are co-linear so that the spacing elements 113 more in parallel planes.

Figure 1C:
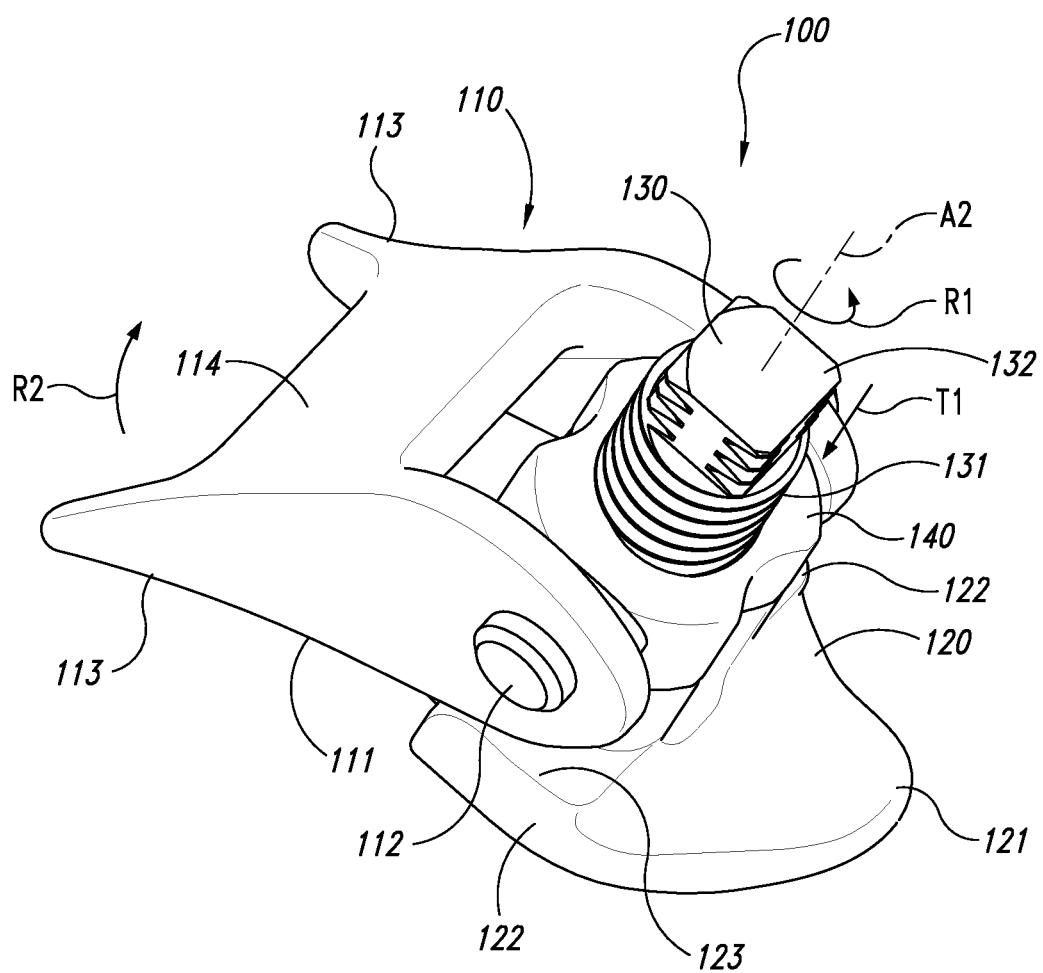
FIG. 1C is a top isometric view of an embodiment of the device shown in FIG. 1B in a representative deployed configuration.

FIG. 1C illustrates the device 100 in the deployed configuration. To achieve the deployed configuration, a practitioner releasably engages a tool (not shown in FIG. 1C) with the tool grip portion 132 of the post 130, e.g., by threading or clamping the tool onto the post 130. The practitioner then rotates the post 130 counterclockwise, as indicated by arrow R1, which drives the actuator device 140 axially away from the tool grip portion 132, as indicated by arrow T1. As the actuator device 140 moves axially, the spinal spacer 110 pivots about the pivot pins 112, outwardly away from the post 130 as indicated by arrow R2. This motion is guided by the sliding contact between the spacer surfaces 111 and the corresponding cam surfaces 123 on each side 122 of the device 100.

Figure 3:
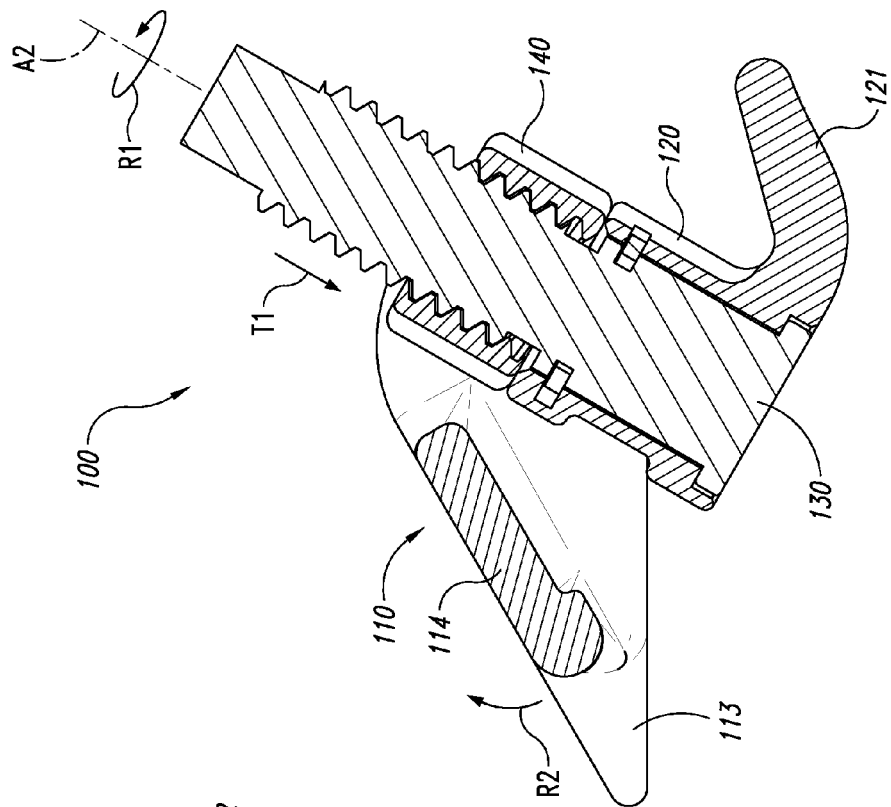
FIG. 3 is a partially schematic, cross-sectional view of the device shown in FIG. 2, illustrating a representative deployed configuration.
Figure 2:
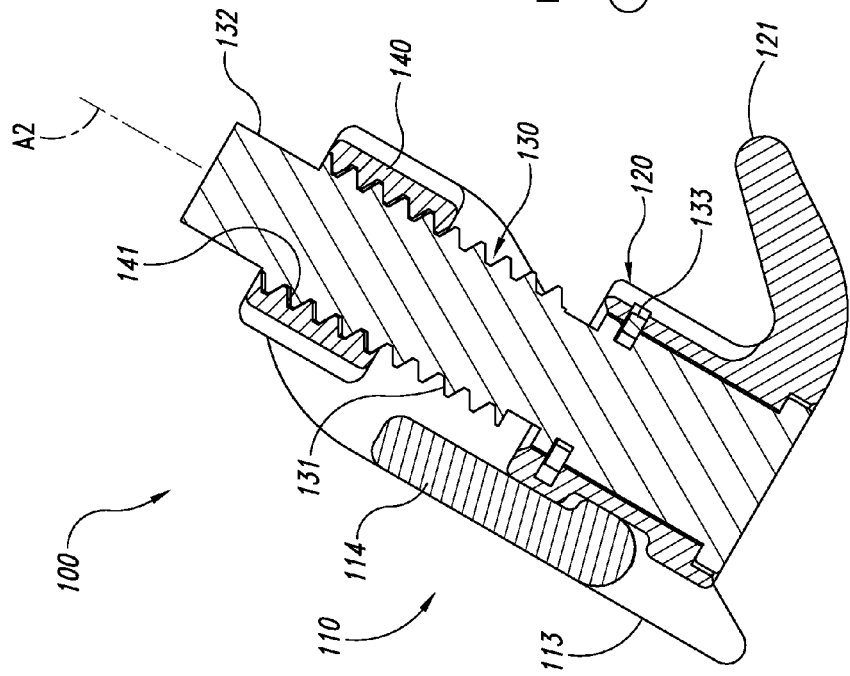
FIG. 2 is a partially schematic, cross-sectional view of the device shown in FIG. 1A, illustrating a representative stowed configuration.

FIGS. 2 and 3 are cross-sectional illustrations of the device 100 shown in FIG. 1A, taken substantially along line 2-2 of FIG. 1A. As shown in FIG. 2, the internal actuator threads 141 of the actuator device 140 are threadably engaged with the external post threads 131 of the post 130. The post 130 includes a retainer ring 133 that fits into a corresponding circumferential slot of the hook member 120. Accordingly, the post 130 can rotate about the second axis A2 relative to the hook member 120.

FIG. 3 illustrates the device 100 after the actuator device 140 has been rotated about the second axis A2 (as indicated by arrow R1) so as to translate axially along the post 130 (as indicated by arrow T1). As the actuator device 140 moves along the second axis A2, the spinal spacer 110 pivots outwardly relative to the post 130, as indicated by R2.

Figure 4:
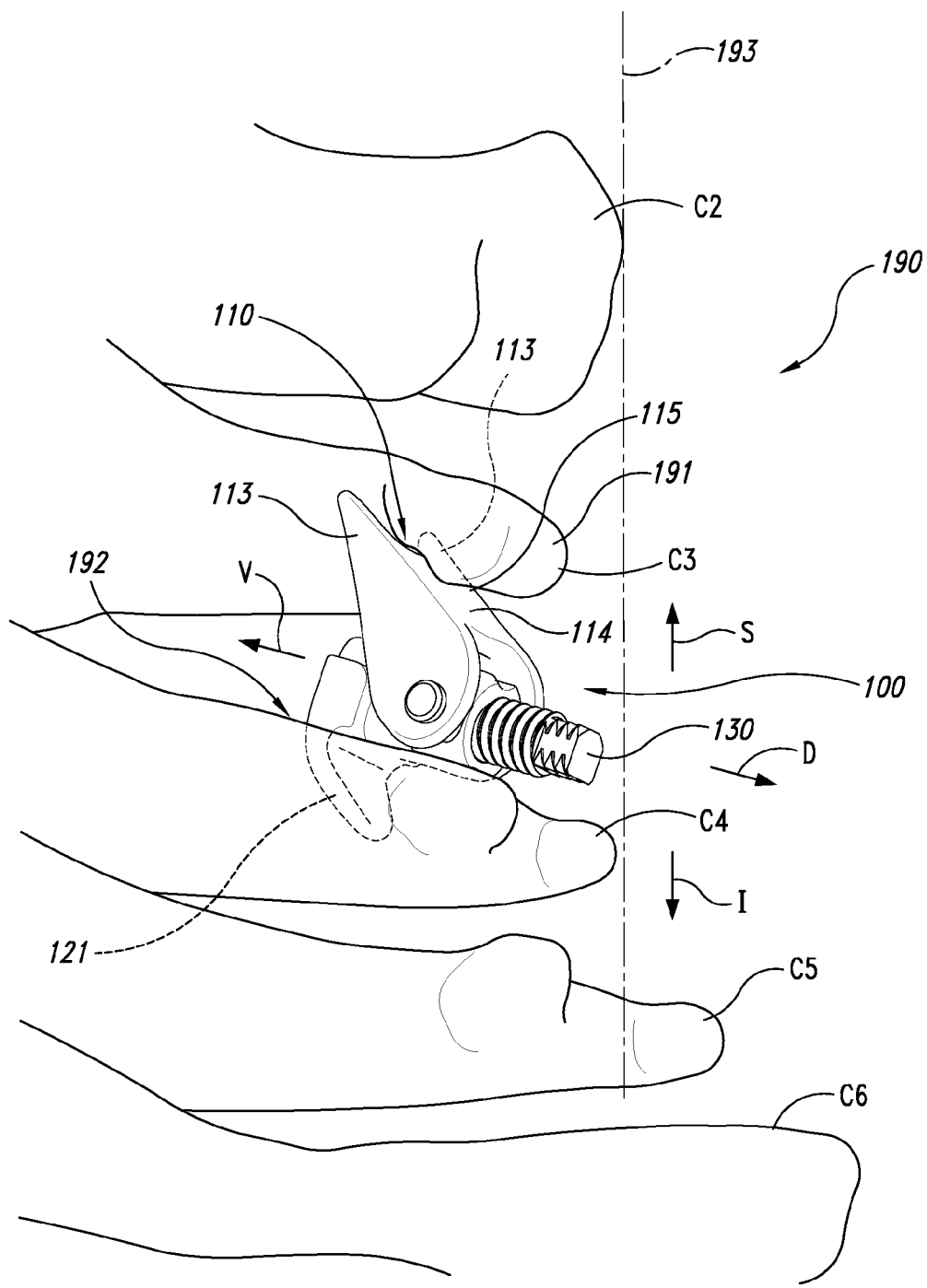
FIG. 4 is an isometric view of a portion of a patient's spine, with the device shown in FIG. 1A positioned between neighboring vertebra in accordance with an embodiment of the disclosure.

FIG. 4 is a partially schematic, isometric illustration of a patient's spine 190, illustrating particular cervical vertebrae C2, C3, C4, C5, and C6. Arrow S identifies the superior direction, arrow I identifies the inferior direction, arrow D identifies the dorsal direction, and arrow V identifies the ventral direction. Prior to inserting the device 100, the practitioner makes a small incision in the patient's skin, along the midline 193. The practitioner makes another incision through the posterior longitudinal ligament (not shown in FIG. 4) to access the vertebrae via a posterior approach. The device 100 is inserted in its stowed configuration between the third cervical vertebra C3 and the fourth cervical vertebra C4 in a dorsal-to-ventral direction, so that the hook 121 is received in the vertebral foramen 192 of the inferior C4 vertebra. The post 130 is then rotated, as discussed above, so as to rotate the spinal spacer 110 in a generally superior direction. The spinal spacer 110 (e.g., the spacing elements 113 and the saddle 114) contact the superior C3 vertebra via one or more of the vertebral contact surfaces 115. In a particular embodiment, the vertebral contact surfaces 115 engage with the spinous process 191 of the superior C3 vertebra. As the spinal spacer 110 rotates, it bears against the spinous process 191 of the superior C3 vertebra, while the hook member 120 bears against the inferior C4 vertebra, thus increasing the spacing between these two neighboring vertebra. At the same time, the hook 121, which is positioned in the vertebral foramen 192, prevents the device 100 from dislodging, or otherwise moving in a significant manner from the position illustrated in FIG. 4. Accordingly, the device 100 can provide pain relief for the patient by providing the proper spacing between the neighboring C3 and C4 vertebra, and can maintain its position at the spine 190. In particular, the spacing elements 113 are positioned on opposing lateral sides of the spinous process 191 to restrict and/or prevent lateral motion of the spinal spacer 110, while the hook 121 (in combination with the contact between the spacing elements 113 and the spinous process 191) restricts and/or prevents motion of the device 100 in the dorsal direction D. The components of the device 100 can be formed from any of a variety of suitable biocompatible materials, including metals (e.g., stainless steel or titanium) and/or plastics, e.g., PEEK.

C. Spinal Spacer Device in Accordance with a Second Embodiment

Figure 5:
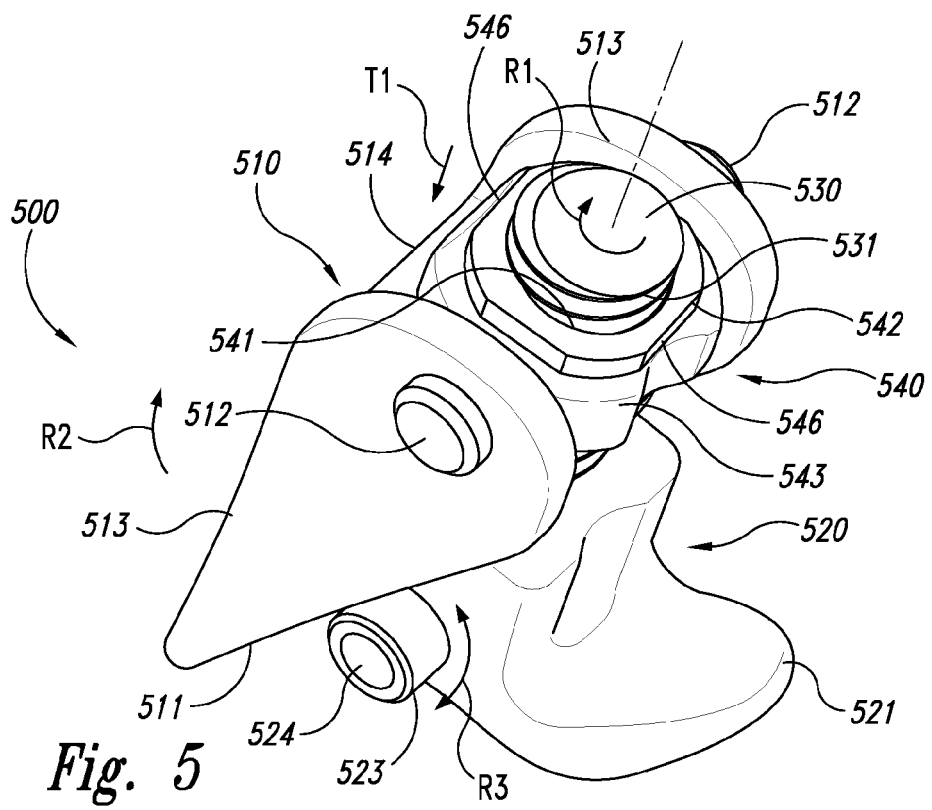
FIG. 5 is a top isometric view of a device having rotating cam surfaces in accordance with another embodiment of the disclosure.

FIG. 5 is a partially schematic, top isometric illustration of a device 500 configured in accordance with a second embodiment of the disclosure. The device 500 can include a hook member 520 having a fixed hook 521 and carrying a post 530 having external post threads 531. The hook member 520 can also include two cam surfaces 523 (one of which is visible in FIG. 5) rotatably secured to the hook member 520 via a cam pin 524. Accordingly, the cam surfaces 523 can rotate relative to the hook member 520. The device 500 can further include a spinal spacer 510 having two wing-shaped spacing elements 513, one positioned on each of two opposing sides of the hook member 520, and connected via a saddle 514. The spinal spacer 510 is moved relative to the hook member 520 via an actuator device 540 that includes an actuator element 542 having internal actuator threads 541 threadably engaged with the external post threads 531 of the post 530. The actuator element 542 fits within an annular opening of a collar 543 so as to rotate relative to the collar 543. The collar 543 is coupled to the spinal spacer 510 with pivot pins 512. Accordingly, a practitioner can engage flat external edges 546 of the actuator element 542 with an actuator tool (not shown in FIG. 5) and rotate the actuator element 542 about the second axis A2, as indicated by arrow R1. As the actuator element 542 rotates, it drives the collar 543 downwardly as indicated by arrow T1. Spacer surfaces 511 of the spacing elements 513 bear against and rotate the corresponding cam surfaces 523, causing the spinal spacer 510 to rotate outwardly as indicated by arrow R2. It is expected that the ability of the cam surfaces 523 to rotate relative to the hook member 520 can reduce the friction between the cam surfaces 523 and the spacing elements 513, thus enhancing the mechanical efficiency with which the spinal spacer 510 is deployed, and/or reducing the likelihood for these components to bind or jam during operation.

Figure 6:
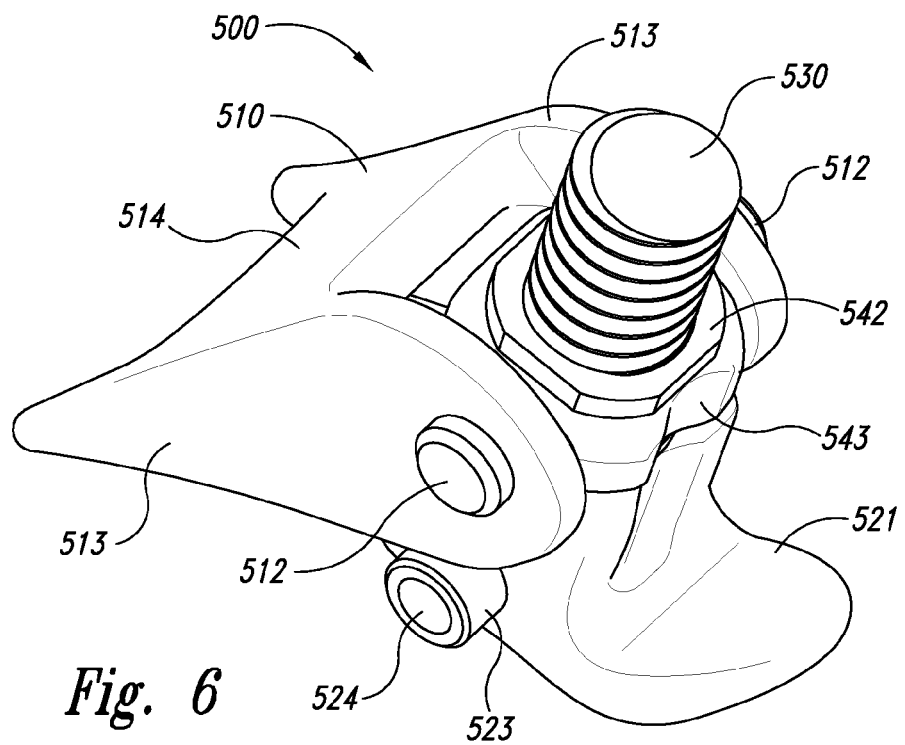
FIG. 6 is a top isometric view of the device shown in FIG. 5, in a deployed configuration.

FIG. 6 is a top isometric view of the device 500 shown in FIG. 5, with the spinal spacer 510 moved to its deployed position. Accordingly, the actuator element 542 has moved downwardly along the post 530, pushing the collar 543 downwardly as well. The spacing elements 513 have rotated outwardly as they bear against and rotate the corresponding cam surfaces 523.

Figure 7:
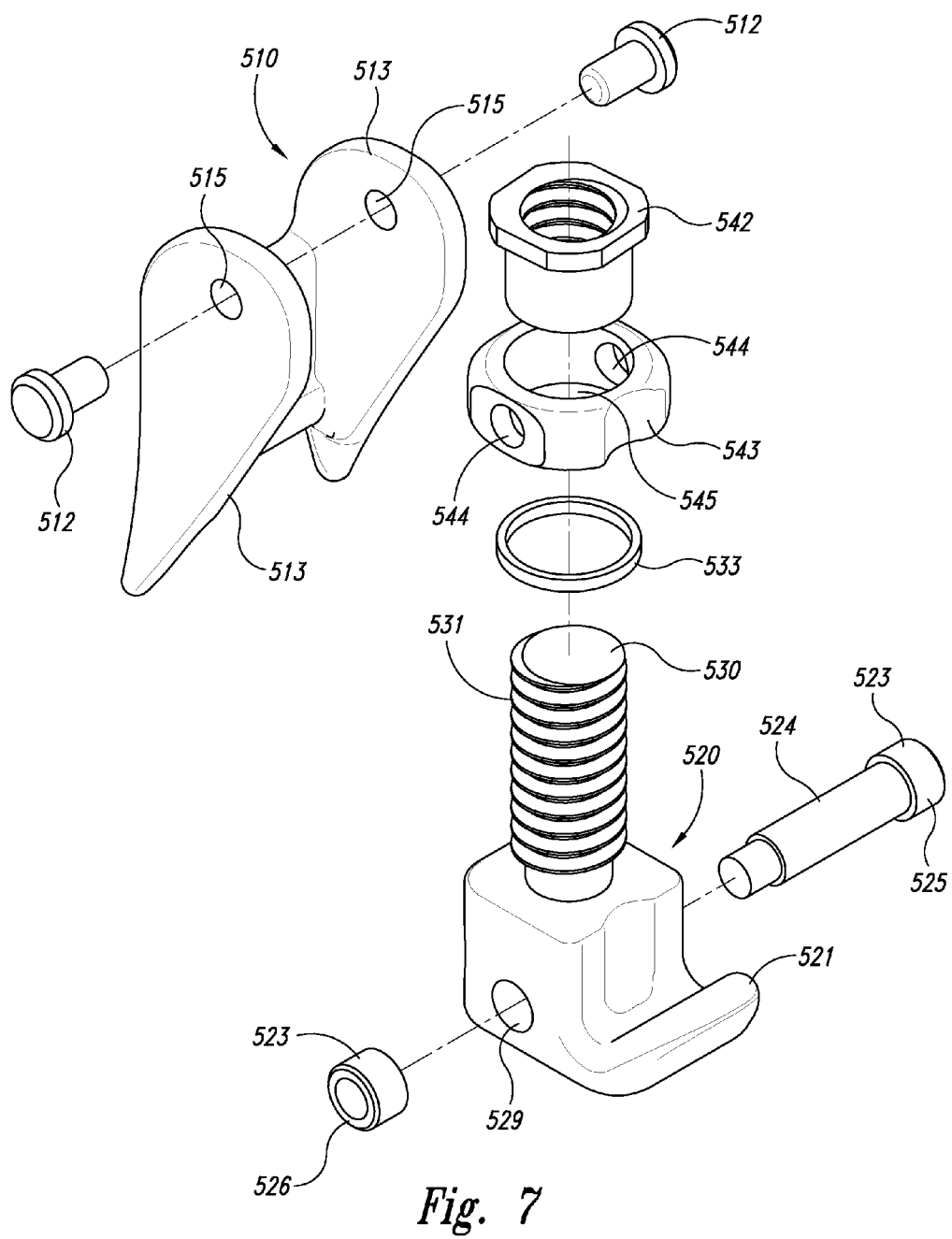
FIG. 7 is a partially schematic, exploded view of components of the device shown in FIGS. 5 and 6.

FIG. 7 is a partially schematic, isometric, exploded view of components forming the device 500 in accordance with an embodiment of the disclosure. As shown in FIG. 7, the hook member 520 and the post 530 are fixed relative to each other. The hook member 520 includes a cam pin hole 529 that receive the cam pin 524 so that the cam pin 524 can rotate relative to the hook member 520. The cam pin 524 includes a head 525 with an outer cylindrical surface that forms one of the cam surfaces 523. The cam pin 524 is attached to a keeper 526 having an outer cylindrical surface that forms the opposite cam surface 523. The collar 543 includes a collar opening 545 which receives the actuator element 542. Once the actuator element 542 is inserted into the collar 543, a retaining ring 533 is attached to the bottom of the actuator element 542 to capture the collar 543 between the retaining ring 533 and the actuator element 542. The actuator element 542 is then threaded onto the post threads 531 of the post 530, and the spinal spacer 510 is attached to the collar 543. The spinal spacer 510 includes holes 515 that are aligned with corresponding collar holes 544 in the collar 543. During assembly, the pivot pins 512 are inserted through the holes 515 in the spinal spacer 510 and attached to the collar 543 via the collar holes 544. Accordingly, the spinal spacer 510 can pivot outwardly relative to the collar 543.

Figure 8:
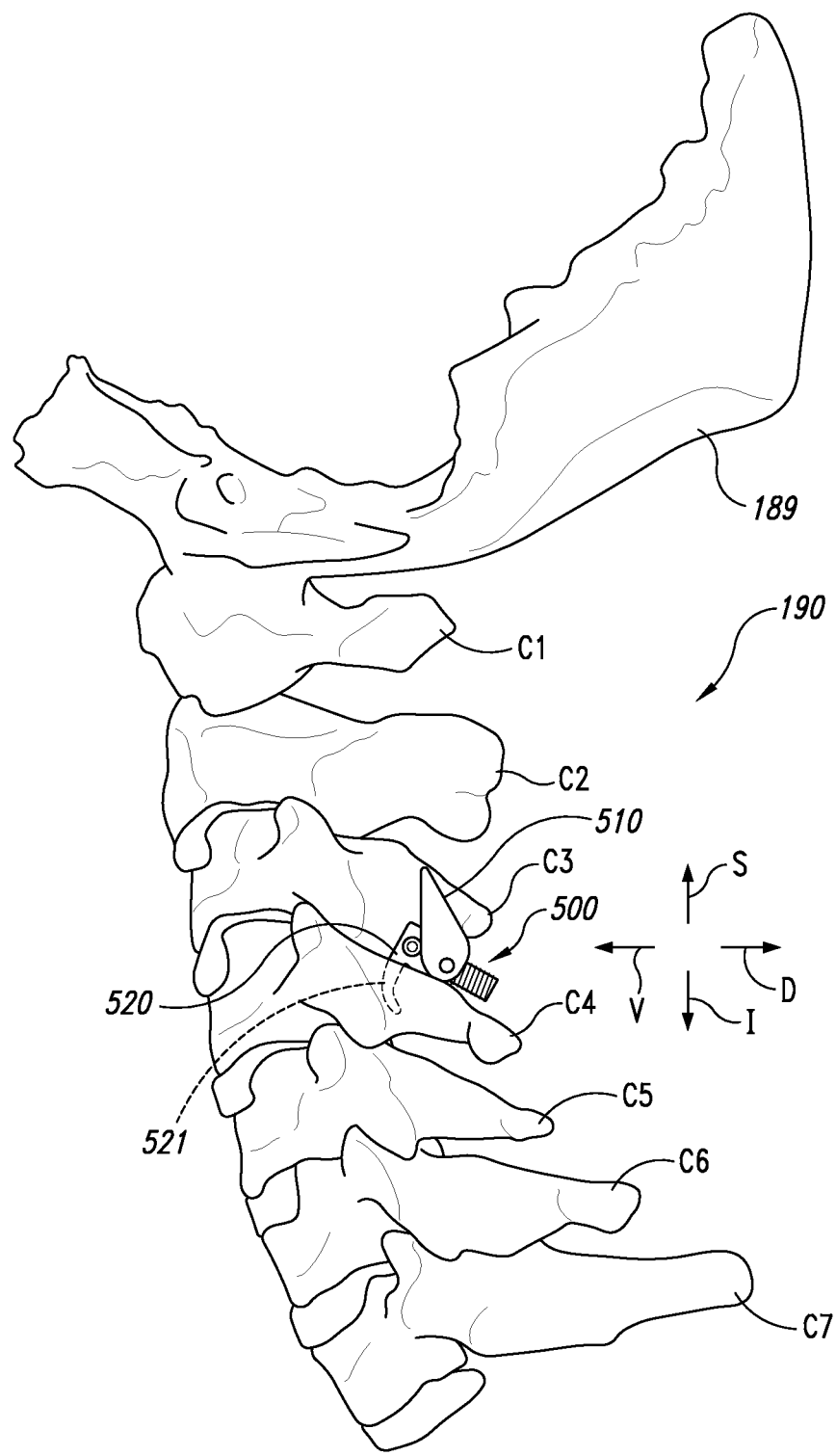
FIG. 8 is a partially schematic side view of the cervical portion of a patient's spine, with an embodiment of the device shown in FIGS. 5-7 inserted between neighboring vertebra in accordance with an embodiment of the disclosure.

FIG. 8 is a partially schematic, side view of the patient's spine 190 and skull 189. The device 500 has been inserted between the third and fourth cervical vertebra C3, C4 and deployed in the manner described above so as to increase or at least maintain the spacing between these two vertebra. The functions provided by the hook member 520, the hook 521, and the spinal spacer 510 are generally similar to those described above with reference to the corresponding elements shown in FIGS. 1A-4.

D. Spinal Spacer Device in Accordance with a Third Embodiment

FIG. 9A is a partially schematic side view of a device 900 configured in accordance with a third embodiment of the disclosure, and shown in its stowed configuration. FIG. 9B is a side view of the device 900 shown in its deployed configuration. Referring to FIGS. 9A and 9B together, the device 900 includes a hook member 920 carrying a hook 921. The hook member 920 can have a distal end 927 with a generally pointed shape to aid in inserting the device 900 into the interspinous space between neighboring vertebra. The hook member 920 carries a post 930 having external post threads 931 that engage with internal threads of an actuator element 942. The actuator element 942 is slidably positioned within a collar 943 to form an actuator device 940 that operates in a manner generally similar to the actuator device 540 described above. A spinal spacer 910 is pivotably attached to the collar 943 via a pair of pivot pins 912, one of which is visible in FIG. 9A. The spinal spacer 910 includes two spacing elements 913, one of which is visible in FIG. 9A, connected to each other with a saddle 914. Each of the spacing elements 913 has an aperture 916 (e.g., a generally slot-shaped aperture) that receives a cam pin 924 and associated cam surface 923 when the spinal spacer 910 is stowed. The aperture 916 is bounded in part by a spacer surface 911 that bears against the corresponding cam surface 923. The apertures 916 allow the corresponding spacing elements 913 to hook around the corresponding cam pins 924 during insertion, reducing or eliminating the likelihood for the spacing elements 913 to deploy inadvertently during insertion.

In FIG. 9B, the spinal spacer 910 has been deployed by rotating the actuator element 942 relative to the post 930, thus driving the collar 943 in a generally ventral/superior direction, which forces the spinal spacer 910 to pivot in a generally superior/dorsal direction as the spacer surfaces 911 bear against the corresponding cam surfaces 923. As discussed above, the hook member 920 and the spinal spacer 910 can accordingly space neighboring vertebra apart from each other, while the hook 921 and spinal spacer 910 prevent or at least restrict motion of the device 900 relative to the patient's spine.

Figure 10B:
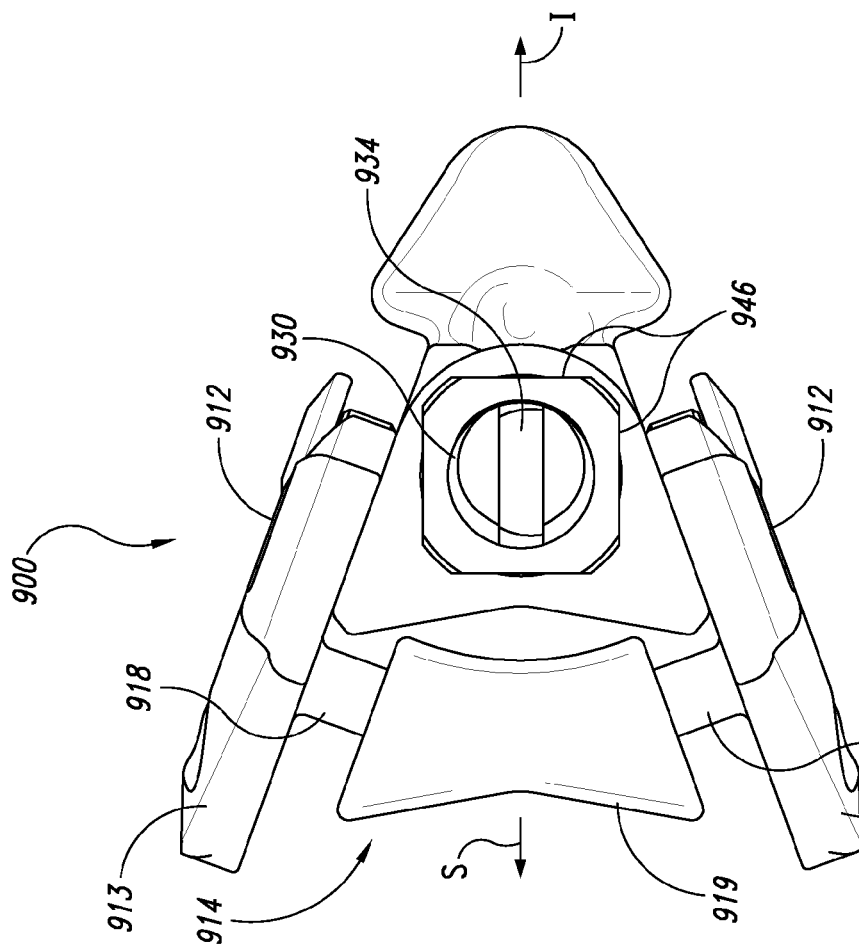
FIGS. 10A and 10B are top views of the device shown in FIGS. 9A and 9B, in a stowed configuration (FIG. 10A) and a deployed configuration (FIG. 10B).
Figure 10A:
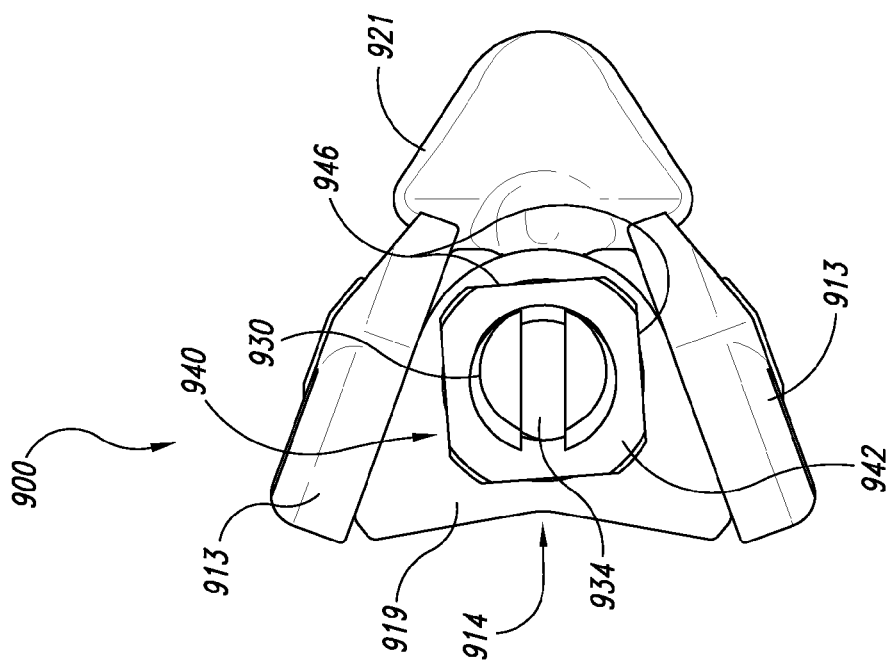

FIGS. 10A and 10B illustrate the device 900 from a generally ventral position in the stowed configuration (FIG. 10A) and in the deployed configuration (FIG. 10B). As shown in FIGS. 10A and 10B, the spacing elements 913 are not positioned parallel to each other, but instead splay outwardly relative to each other in a generally superior direction. The pivot pins 912 are not collinear and, accordingly, the spacing elements 913 rotate in non-parallel planes. This arrangement is expected to more closely track the shape of the dorsal side of the superior vertebra, which also splays outwardly around the vertebral foramen. Accordingly, it is expected that this arrangement will provide more contact and/or more secure contact between the device 900 and the vertebra between which the device is placed. In order to accommodate the relative motion between the spacing elements 913 as the spinal spacer 910 is deployed, the saddle 914 can include a centrally located saddle element 919, which is supported in place by two saddle pins 918 (FIG. 10B), each of which extends inwardly from a corresponding one of the spacing elements 913. As the spacing elements 913 pivot, the saddle pins 918 can move outwardly within corresponding apertures in the saddle element 919, so that the saddle element 919 does not cause the spinal spacer 910 to bind as it pivots. The saddle element 919 and the saddle pins 918 can be shaped and configured so that the saddle element 919 remains in a central location as the spacing elements 913 move. For example, each of the saddle pins 918 can terminate in a spherical bulb or ball. Accordingly, the saddle element 919 can aid in centering the device 900 on the midline of the patient's spine, despite vertebral shapes that may vary from one patient to another.

As is also shown in FIGS. 10A and 10B, the post 930 can include an alignment slot 934, and the actuator element 942 can include outwardly facing edges 946. The alignment slot 934 can be used to align an actuation tool relative to the post 930, and the edges 946 can engage with the actuation tool to facilitate rotating the actuator device 942 relative to the post 930. Further details of this operation are described below with reference to FIGS. 11A-11E.

Figure 11A:
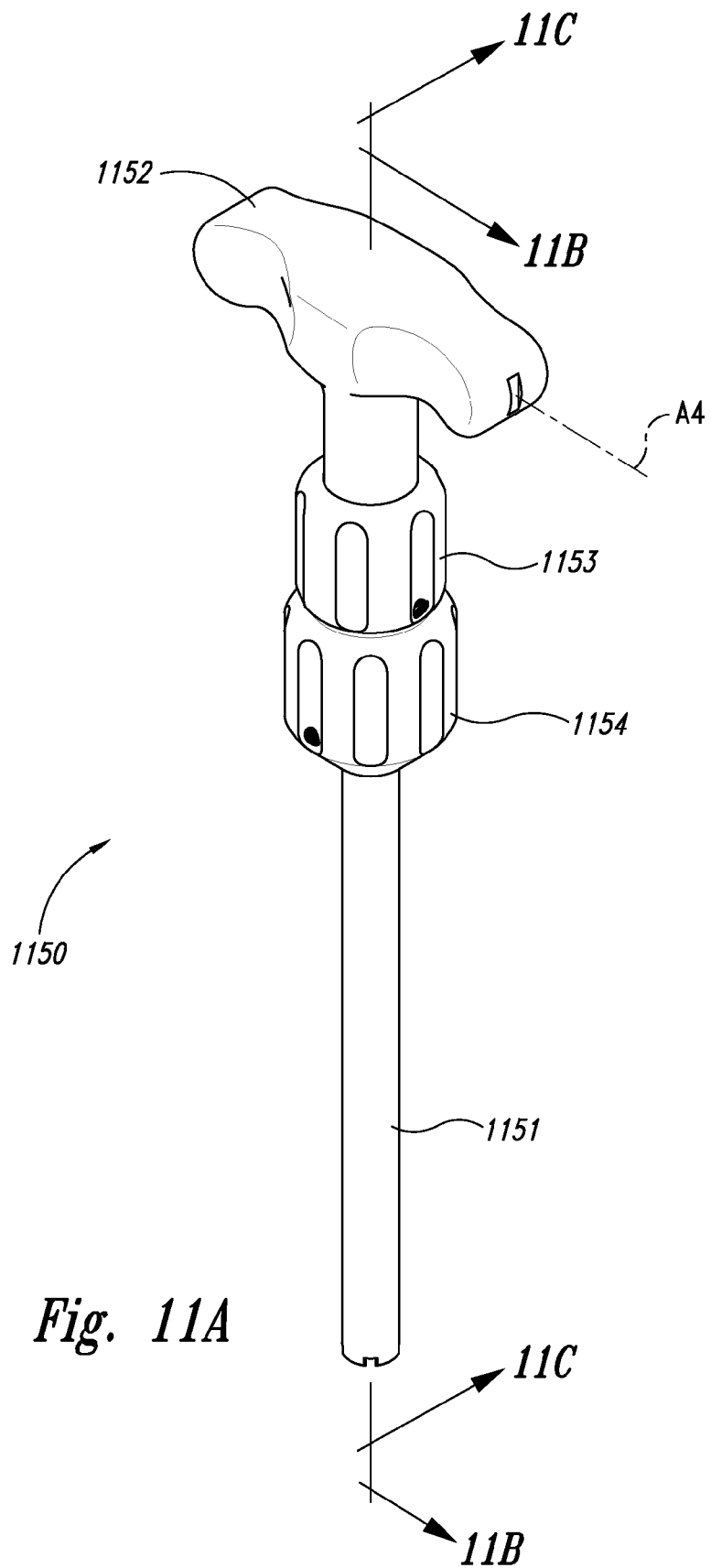
FIG. 11A is a partially schematic, view illustration of an actuator tool configured to actuate the device shown in FIGS. 9A-10B in accordance with an embodiment of the disclosure.

E. Actuation Tool for Use with a Device in Accordance with the Third Embodiment FIG. 11A is an isometric, partially schematic view of an actuator tool 1150 configured to insert and deploy a spinal spacer device, for example, the device 900 described above with reference to FIGS. 9A-10B. In one aspect of this embodiment, the actuator tool 1150 includes a shaft assembly 1151, a handle 1152, a first knob 1153, and a second knob 1154. The handle 1152 can be elongated along a handle axis A4 for ease of operation, and to facilitate aligning the tool 1150. The handle 1152, the first knob 1153, and the second knob 1154 are connected to and operate concentrically arranged components of the shaft assembly 1151, as described further below.

Figure 11C:
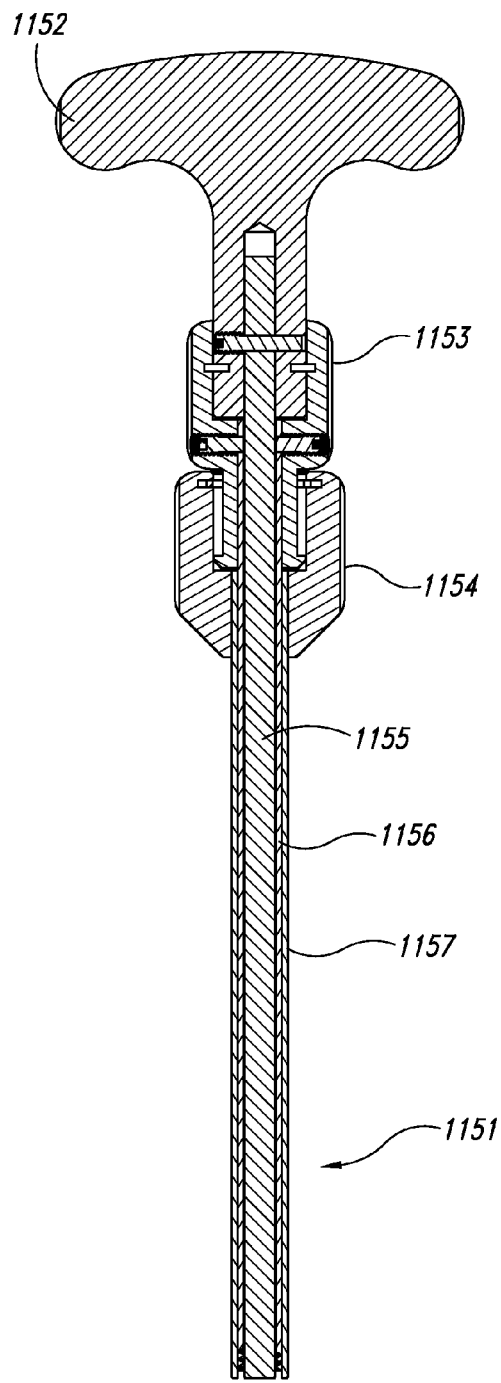
FIGS. 11B and 11C are cross-sectional illustrations of the tool shown in FIG. 11A, taken substantially along lines 11B-11B and 11C-11C, respectively.
Figure 11B:
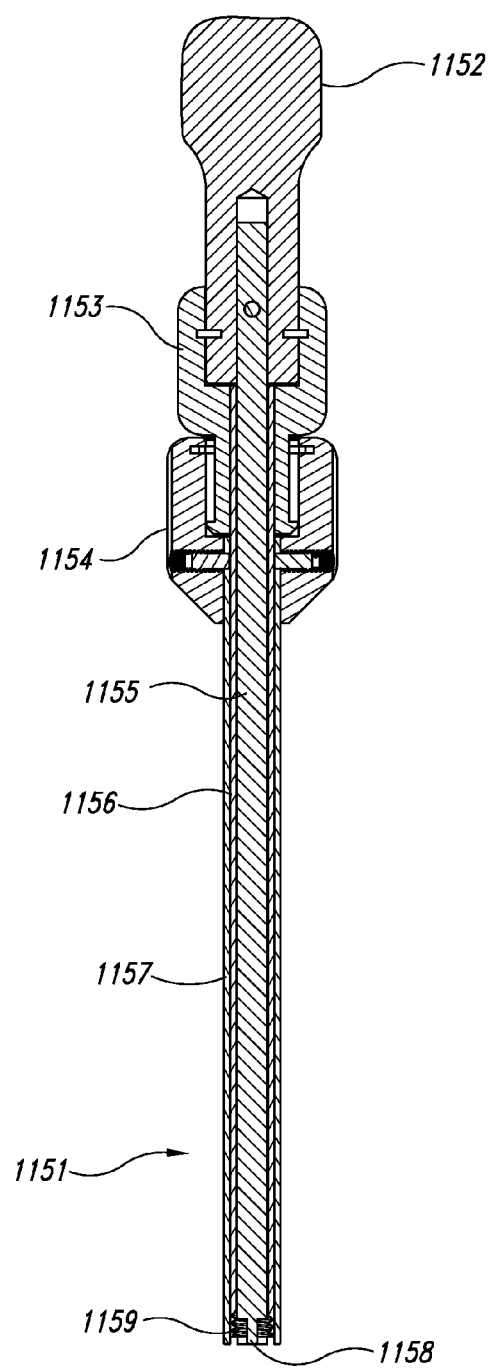

FIG. 11B is a partially schematic, cross-sectional illustration of the actuator tool 1150, taken substantially along line 11B-11B of FIG. 11A. FIG. 11C is a partially schematic, cross-sectional illustration of the actuator tool 1150, taken substantially along line 11C-11C of FIG. 11A. Referring to FIGS. 11B and 11C together, the shaft assembly 1151 includes an actuator shaft 1157 connected to the second knob 1154 and an attachment shaft 1156 positioned annularly inwardly from the actuator shaft 1157 and connected to the first knob 1153. The shaft assembly 1151 further includes an alignment shaft 1155 positioned annularly inwardly from the attachment shaft 1156 and attached to the handle 1152. Accordingly, when a practitioner rotates the handle 1152, the alignment shaft 1155 rotates. When the practitioner rotates the first knob 1153, the attachment shaft 1156 rotates, and when the practitioner rotates the second knob 1154, the actuator shaft 1157 rotates. Referring to FIG. 11B, the attachment shaft 1156 includes internal threads 1159 for attaching to the device 900, and the alignment shaft 1155 includes an alignment tab 1158 for aligning the actuator tool 1150 properly with the device 900. These features are described further below with reference to FIG. 11D.

FIG. 11D is a bottom isometric view, looking upwardly at the distal end portion of the shaft assembly 1151 described above with reference to FIGS. 11A-11C. As shown in FIG. 11D, the alignment tab 1158 is elongated along a tab axis A3 and extends outwardly from a lower portion of the alignment shaft 1155. The attachment shaft 1156 includes internal threads 1159 and can rotate relative to the alignment shaft 1155. The actuator shaft 1157 includes inwardly facing engagement surfaces 1160 and can rotate relative to both the attachment shaft 1156 and the alignment shaft 1155.

The operation of the actuator tool 1150 is now described with reference to FIGS. 11D and 11E, and also with reference to the device 900 upon which it operates, which was described above with reference to FIGS. 9A-10B, and which is shown again in FIG. 11F. When the tool 1150 is in a starting configuration, the tab axis A3 of the alignment tab 1158 shown in FIG. 11D is aligned parallel with the handle axis A4 of the handle 1152 shown in FIG. 11E. Accordingly, the operator can align the handle axis A4 with the alignment slot 934 of the device 900 shown in FIG. 11F. Doing so will automatically align the alignment tab 1158 (FIG. 11D) with the alignment slot 934 of the device 900 (FIG. 11F). With the alignment tab 1158 placed within the alignment slot 934, the practitioner rotates the first knob 1153, thereby engaging the internal threads 1159 of the attachment shaft 1156 with the external post threads 931 of the post 930. This operation releasably secures the device 900 to the actuator tool 1150, as is shown in FIG. 11E. This operation also advances the engagement surfaces 1160 of the actuator shaft 1157 axially so that they are positioned adjacent to the corresponding edges 946 of the actuator device 940. Accordingly, when the operator rotates the second knob 1154, the attached actuator shaft 1157 rotates the actuator element 942. The practitioner continues to rotate the second knob 1154 to advance the actuator element 942 along the post 930, thereby deploying the spinal spacer 910 to the deployed position shown in FIG. 9B.

F. Spinal Spacer Device in Accordance with a Fourth Embodiment

FIGS. 12A and 12B are partially schematic, side elevation views of a device 1200 configured in accordance with a fourth embodiment of the disclosure, shown in a stowed configuration (FIG. 12A) and a deployed configuration (FIG. 12B). In one aspect of this embodiment, the device includes a deployable hook. In another aspect of this embodiment, the post is internally threaded and the actuator is externally threaded. Further details of these features are described below.

Referring to FIGS. 12A and 12B together, the device 1200 includes a hook member 1220 having a hook 1221 that is folded (e.g., generally parallel to the second axis A2) when the device 100 is in its stowed configuration. The hook 1221 is unfolded so as to extend along the first axis A1 when the device 1200 is deployed. The hook member 1220 has a fixed position relative to a generally cylindrical housing 1280, which has a housing aperture 1282 (e.g., a generally cylindrical cavity) and a housing cap 1281 over the end of the housing aperture 1282. An actuator device 1240 (visible in FIG. 12B) rotates within the housing 1280 to deploy a spinal spacer 1210.

The spinal spacer 1210 can include two spacing elements 1213 (one is visible in FIGS. 12A, 12B) pivotably coupled to the actuator device 1240 via corresponding pivot pins 1212. Each spacing element 1213 has a spacer surface 1211 that bounds, in part, an aperture 1216. Each spacer surface 1211 bears against a corresponding cam surface 1223 which can rotate relative to the hook member 1220. In a particular embodiment, the cam surface 1223 is carried by a cam pin 1224 which is attached to an annular keeper 1226 to limit the lateral motion of the corresponding spacing element 1213. In the stowed configuration, the spacing element 1213 is generally aligned with the second axis A2, and the cam surface 1223 is received in the aperture 1216. When the device 1200 is changed to the deployed configuration (shown in FIG. 12B), the hook 1221 deploys outwardly, and the spacing elements 1213 deploy outwardly, generally in the opposite direction.

Figures 13A, 13B:
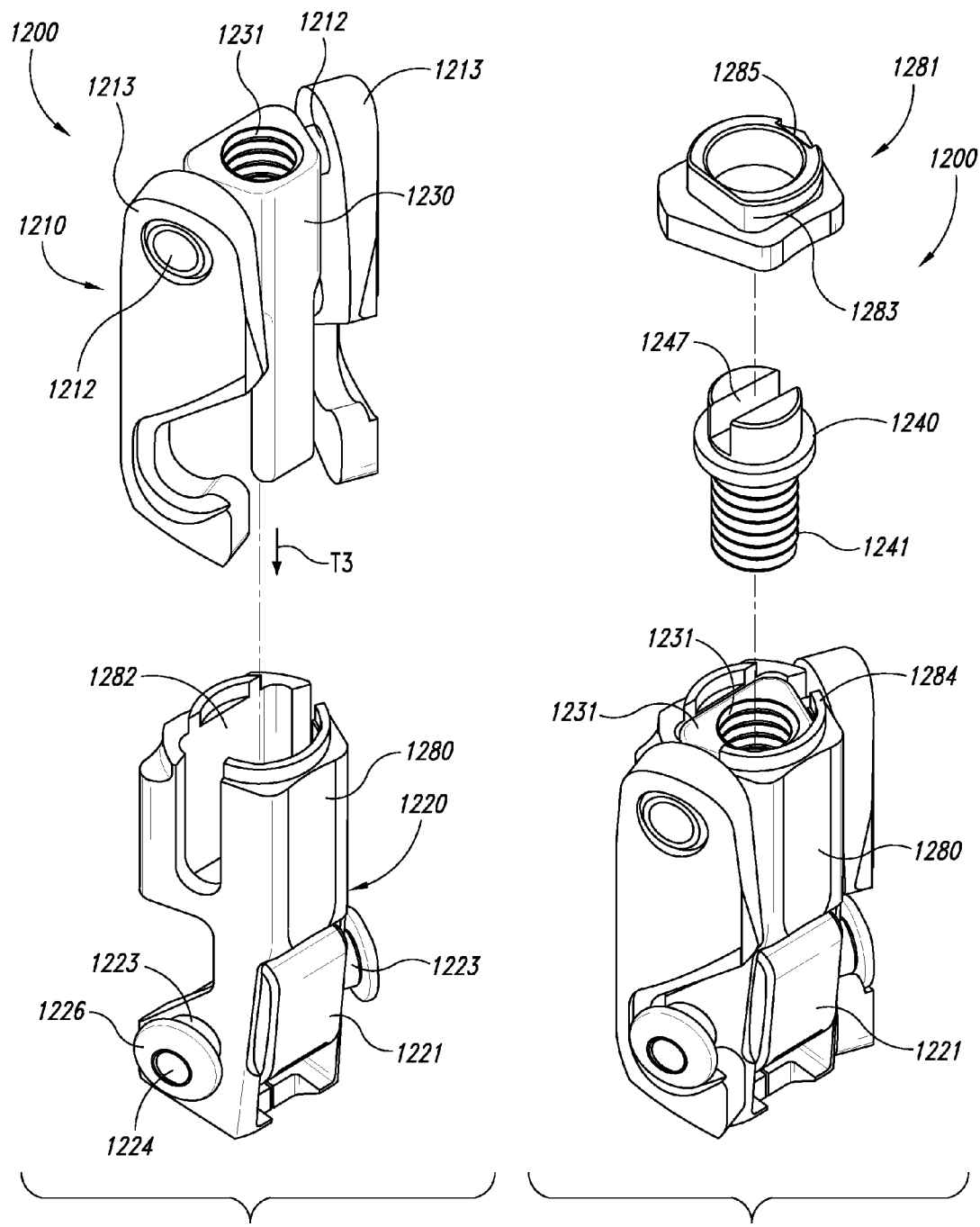
FIGS. 13A and 13B illustrate components of the device shown in FIGS. 12A and 12B during sequential stages of assembly.

FIGS. 13A and 13B illustrate the device 1200 during two steps in an overall component assembly process. Referring first to FIG. 13A, the spacing elements 1213 of the spinal spacer 1210 are pivotably connected to the post 1230 with corresponding pivot pins 1212. The spacing elements 1213 are non-parallel to each other, and splay outwardly as they deploy, in a manner generally similar to that described above with reference to FIGS. 10A-10B. The post 1230, which has internal post threads 1231, is inserted into the housing aperture 1282, as indicated by arrow T3.

Referring now to FIG. 13B, the post 1230 has been inserted into the housing aperture 1282. The actuator device 1240, with its external actuator threads 1241, is then threadably engaged with the post threads 1231. The actuator device 1240 includes an alignment slot 1247 for alignment with an actuation tool, described below. After the actuator device 1240 has been threadably engaged with the post 1230, the housing cap 1281 is positioned over the actuator device 1240, and is sealed to a corresponding cap lip 1284 extending upwardly from the housing 1280 (e.g., with a thermal weld or an adhesive). Accordingly, the actuator device 1240 is captured within the housing 1280, but is free to rotate relative to the housing 1280. A cutout 1285 in the housing cap 1281 is used to align an insertion tool, and an engagement slot 1283 receives the tool, as described later with reference to FIG. 17C.

FIGS. 14A and 14B are partially schematic, cross-sectional illustrations of the assembled device 1200 in a stowed configuration (FIG. 14A) and a deployed configuration (FIG. 14B). Referring to FIGS. 14A and 14B together, the device 1200 is changed from the stowed configuration to the deployed configuration by inserting a tool having a flat blade (generally like a standard screwdriver) into the tool slot 1247 and rotating the tool about the second axis A2, as indicated by arrow R1. As the actuator device 1240 rotates about the second axis A2, it drives the post 1230 downwardly as shown in FIG. 14B. The post 1230 includes a hook actuator 1235 that is received in a hook slot 1228 of the hook 1221. As the post 1230 and the hook actuator 1235 move downwardly, the hook actuator 1235 drives the hook 1221 to rotate outwardly to its deployed position, shown in FIG. 14B. At the same time, the spacing elements 1213 (one of which is visible in FIGS. 14A and 14B) rotate outwardly to their deployed positions as they pivot relative to the post 1230 about the pivot pins 1212 (FIG. 12B), and slide relative to the cam surfaces 1223 (FIG. 12B). In one embodiment, the motion of the spacing elements 1213 can be delayed relative to the motion of the hook 1221 because part of the spacer surface 1211 (best shown in FIG. 12A) is aligned generally parallel to the second axis A2. Accordingly, the spacing elements 1213 can remain aligned with the second axis A2 until the upper surface of the aperture 1216 (shown sloping slightly upwardly and to the right in FIG. 12A) engages the cam surface 1223. In other embodiments, the motion of the hook 1221 and the spacing elements 1213 can be simultaneous, or can have other timing sequences.

FIGS. 15A and 15B illustrate the device 1200 in the stowed and deployed configurations, respectively, from a posterior or dorsal position. As shown in FIGS. 15A and 15B, the spacing elements 1213 pivot in a generally superior direction S while the hook 1221 deploys in a generally inferior direction I, as the actuator device 1240 is rotated in the direction indicated by arrow R1. The spinal spacer 1210 can include a saddle 1214, including a saddle element 1219 supported by corresponding saddle pins 1218. As discussed above with reference to FIGS. 9A-10B, the saddle pins 1218 can retain the saddle 1214 in a central position, while partially withdrawing from or otherwise moving relative to the saddle element 1219 as the spacing elements 1213 splay outwardly during deployment.

Figure 16A:
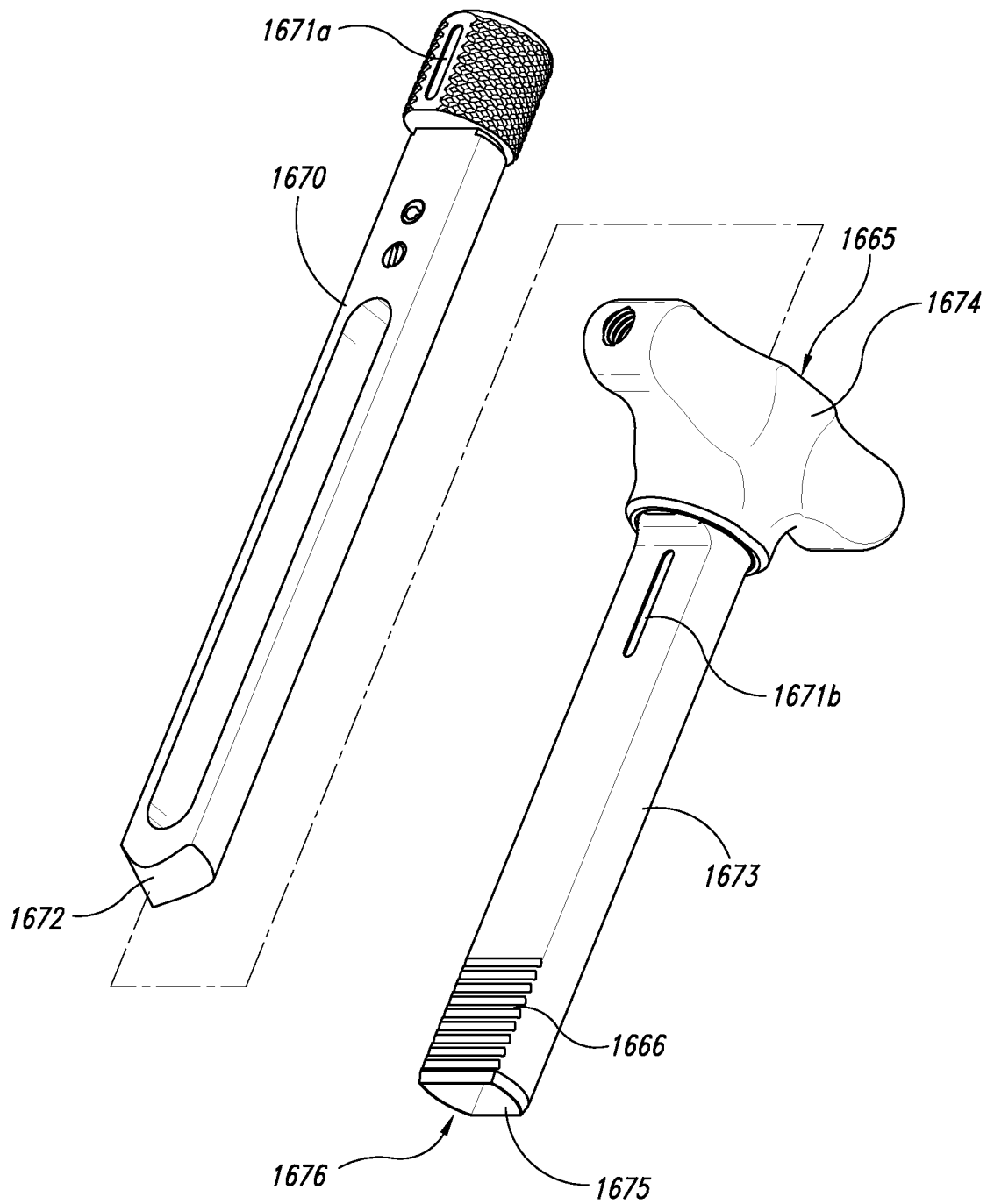
FIG. 16A is a partially schematic, isometric illustration of a cannula and cannula insertion tool configured to implant a device in accordance with an embodiment of the disclosure.

G. Insertion Tool for Use with a Device in Accordance with the Fourth Embodiment FIG. 16A is a partially schematic, side isometric view of a cannula 1673 and an associated cannula insertion tool 1670. The cannula 1673 provides a temporary channel into the patient's intervertebral space for inserting a spinal spacer device, such as the device 1200 described above with reference to FIGS. 12A-15B. The cannula insertion tool 1670 includes features for inserting the cannula 1673, after which it can be removed to allow the spinal spacer device to be inserted through the cannula 1673. The cannula 1673 can include a handle 1674 and a lumen 1675 that extends from a proximal opening 1665 located at the handle 1674 to a distal opening 1676. The cannula 1673 can further include roughness features 1666 toward the distal opening 1676 that aid in holding the cannula 1673 in place, and an alignment mark 1671b for alignment with the cannula insertion tool 1670 and/or other elements.

Figure 16B:
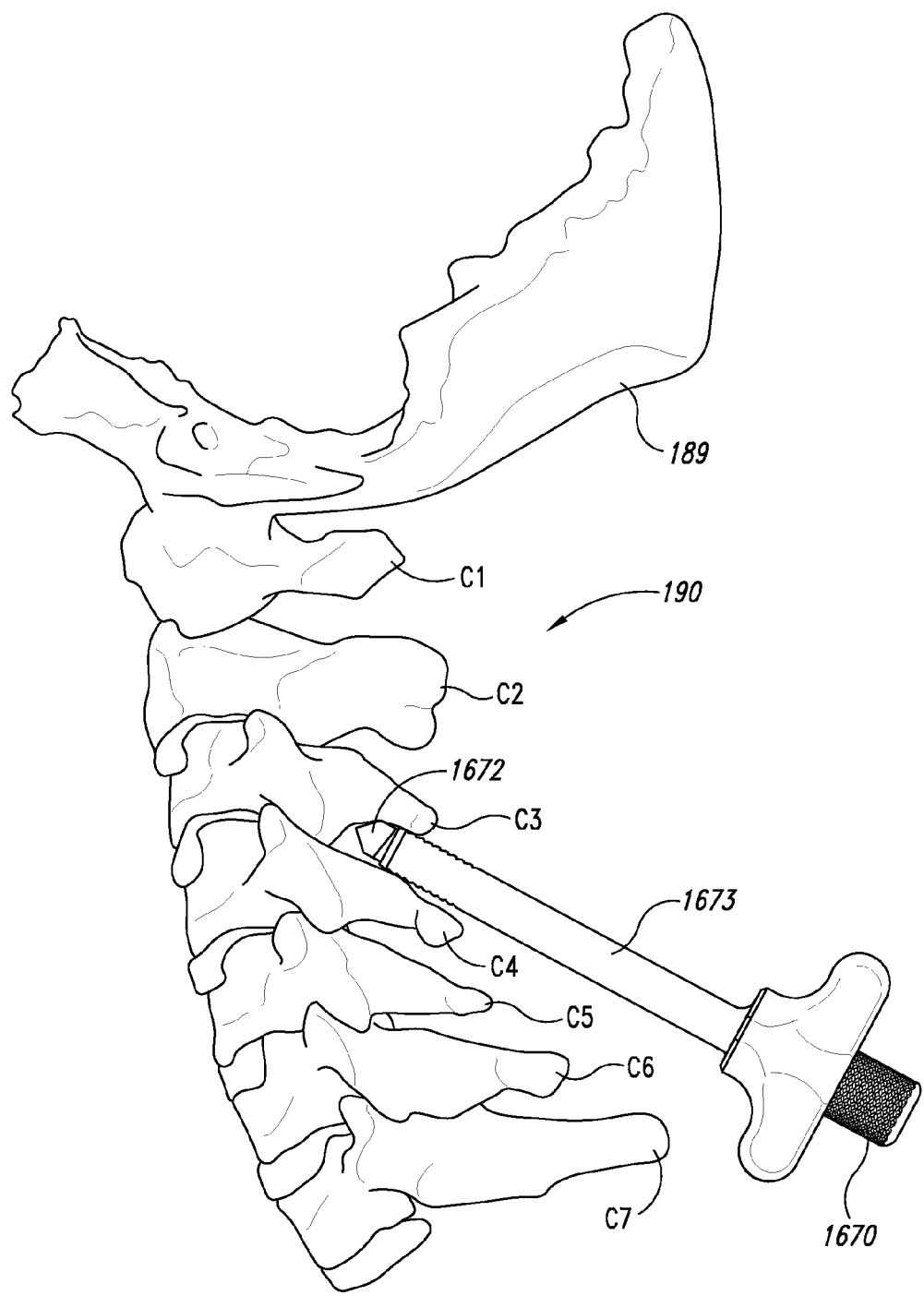
FIG. 16B is a partially schematic, side view of the cannula and cannula insertion tool shown in FIG. 16A, positioned between neighboring vertebra of a patient's spine.

The cannula insertion tool 1670 can include a penetrating tip 1672 and a corresponding alignment mark 1671a that the practitioner aligns with the alignment mark 1671b of the insertion tool 1670. In operation, the practitioner aligns the two marks 1671a, 1671b and inserts the penetrating tip 1672 into the lumen 1675 through the proximal opening 1665. The practitioner moves the cannula insertion tool 1670 through the lumen 1675, until the penetrating tip 1672 extends outwardly from the distal opening 1676. In preparation for inserting the cannula 1673, the practitioner can make an incision through the patient's skin, and can make a further incision through the patient's spinous ligament. Referring now to FIG. 16B, with the insertion tool 1670 inserted in the cannula 1673, and the penetrating tip 1672 extending outwardly from the cannula 1673, the practitioner drives the penetrating tip 1672 between neighboring vertebra (e.g., cervical vertebra C3 and C4), to lodge the cannula 1673 between these vertebra. The practitioner then removes the insertion tool 1670 from the cannula 1673, leaving the cannula 1673 in place.

Figure 17A:
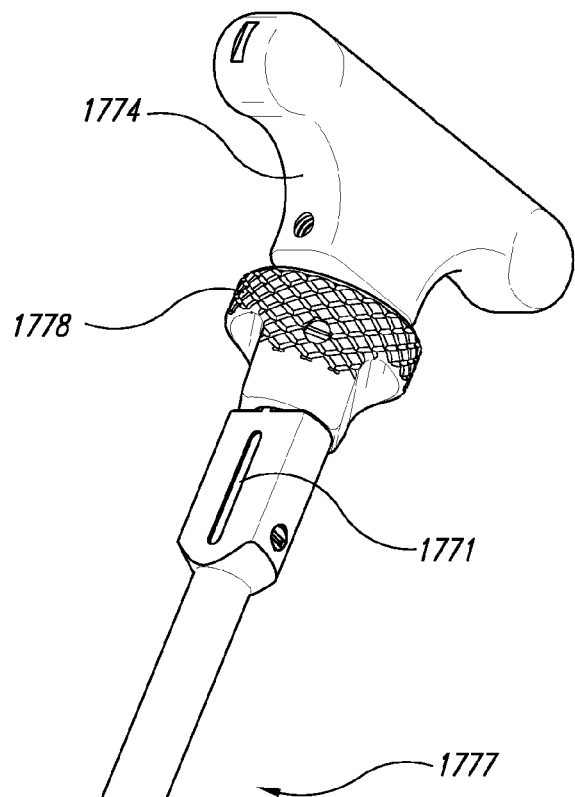
FIG. 17A is a partially schematic, isometric illustration of a device insertion tool configured in accordance with an embodiment of the disclosure.

FIG. 17A illustrates a device insertion tool 1777, which can be releasably engaged with a spinal spacer device (e.g., the device 1200 described above) and then inserted into the cannula 1673 (FIG. 16B) to deploy the device between neighboring vertebra. In a particular embodiment, the device insertion tool 1777 includes an alignment mark 1771 which is aligned with a corresponding alignment mark 1671b of the cannula 1673. The device insertion tool 1777 includes an internal shaft 1769 which is rotatably controlled by a handle 1774. The distal end of the shaft 1769 includes a head 1768 that engages the device 1200. The distal end of the shaft 1769 has multiple shaft sections 1763 (e.g., four). The shaft sections 1763 are separated by axial slots 1762 so that the shaft sections 1763 can flex outwardly relative to each other when the head 1768 engages the device 1200. An external sleeve 1779 is positioned annularly around the shaft 1769, and can slide down over the shaft sections 1763 to prevent the sections 1763 from flexing after the device 1200 is engaged. The sleeve 1779 is controlled by a locking knob 1778.

Figure 17B:
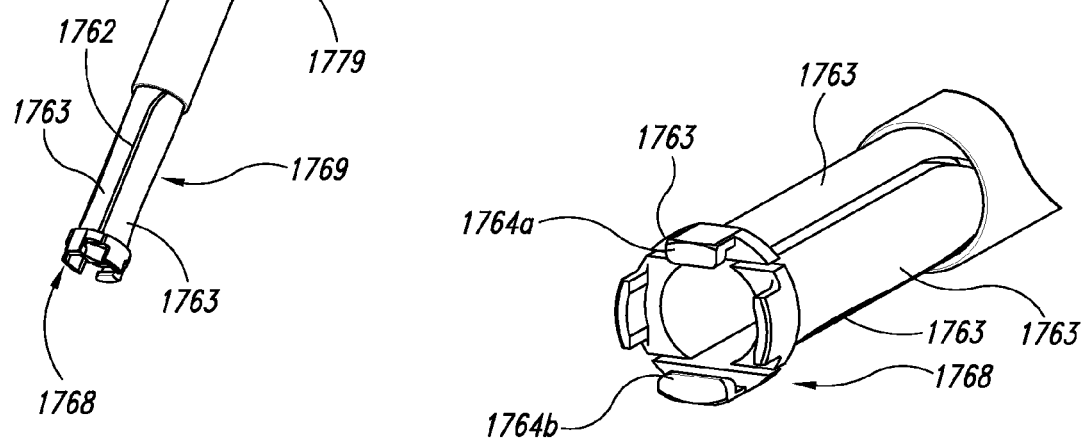
FIG. 17B is a partially schematic, bottom isometric view of a distal end of the device insertion tool shown in FIG. 17A.

FIG. 17B is a partially schematic, isometric view of the distal end of the shaft 1769 shown in FIG. 17A, illustrating the head 1768. The head 1768 can include multiple tabs 1764 (two are shown as a first tab 1764a and a second tab 1764b), each carried by a corresponding one of the sections 1763. The tabs 1764 can engage with the spacer device, as described below with reference to FIG. 17C.

Figure 17C:
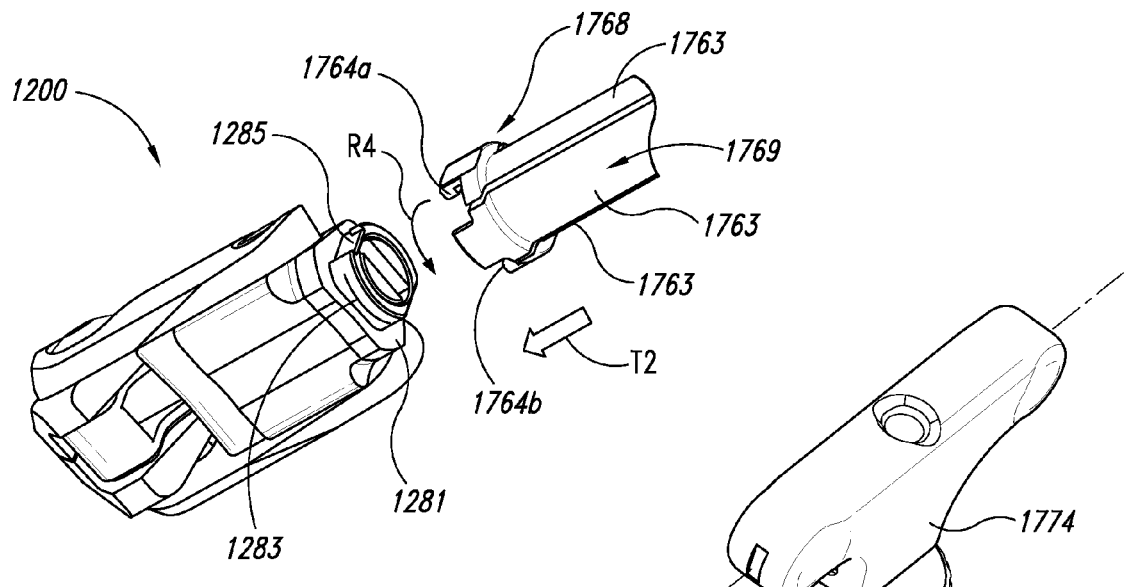
FIG. 17C is a partially schematic, side isometric view of the distal end of the device insertion tool shown in FIG. 17B, in position to engage with a device in accordance with an embodiment of the disclosure.

FIG. 17C illustrates the head 1768 of the shaft 1769, positioned adjacent to the spacer device 1200. The first tab 1764*a* is configured so that it can only be placed over the housing cap 1281 when it is properly aligned with a corresponding cutout 1285 in the housing cap 1281. The second tab 1764*b* is positioned opposite from the first tab 1764*a*. In operation, the practitioner aligns the first tab 1764*a* with the cutout 1285 and advances the head 1768 over the outwardly projecting portion of the housing cap 1281, as indicated by arrow T2. The practitioner then rotates the shaft 1769 as indicated by arrow R4 (e.g., by about 90°) so that the tabs 1764*a*, 1764*b* enter corresponding engagement slots 1283 (one of which is visible in FIG. 17C) in the housing cap 1281. As the tabs 1764*a*, 1764*b* rotate around the squared-off portions of the housing cap 1281, the shaft sections 1763 deflect outwardly and then inwardly until the tabs 1764*a*, 1764*b* settle into the corresponding engagement slots 1283. The sleeve 1779 (not visible in FIG. 17C) is then deployed over the shaft sections 1763 to prevent further flexing, as described below with reference to FIGS. 17F-17G.

Figure 17D:
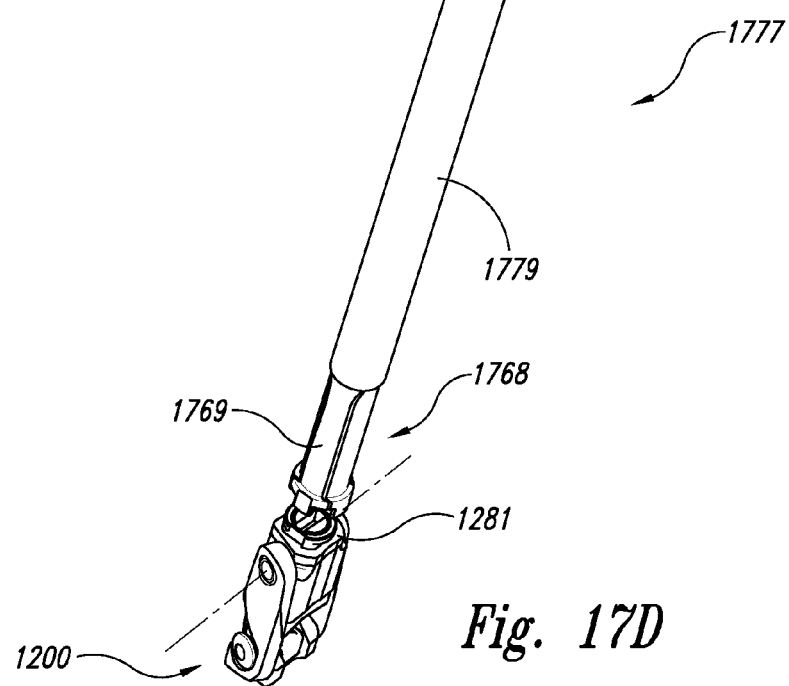
FIG. 17D is a top isometric view of the device insertion tool and device shown in FIG. 17C.
Figures 17E, 17F:
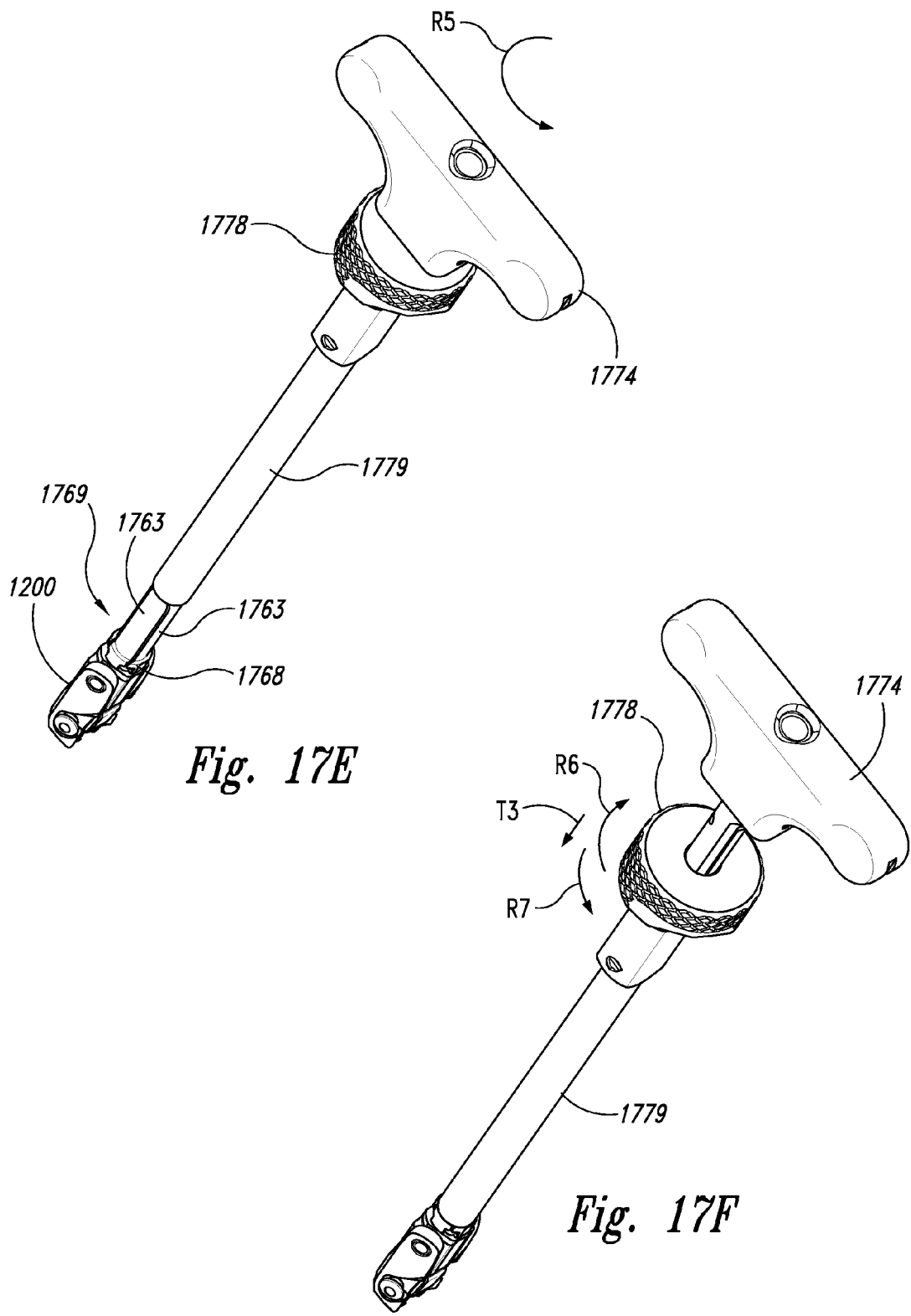
FIG. 17E illustrates the device insertion tool attached to the device shown in FIG. 17D.
FIG. 17F illustrates the device insertion tool in locked engagement with the device shown in FIG. 17E.
Figure 17G:
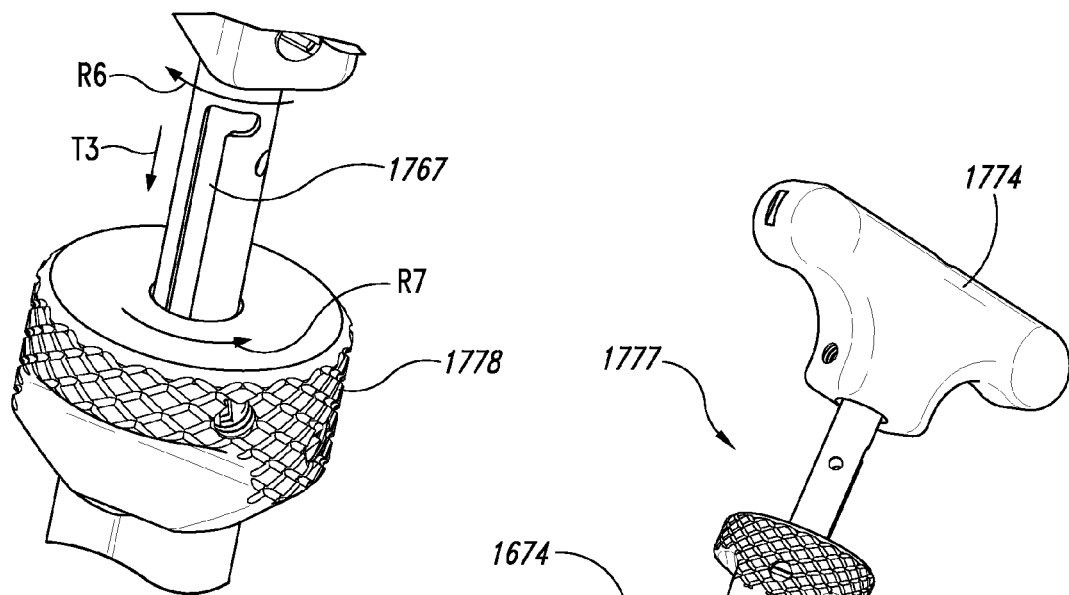
FIG. 17G illustrates the operation of a locking mechanism of the device insertion tool shown in FIG. 17F.

FIG. 17D illustrates the device insertion tool 1777 with the handle 1774 properly aligned with the device 1200, just prior to engaging the head 1768 with the housing cap 1281. FIG. 17E illustrates the device insertion tool 1777 with the head 1768 engaged with the device 1200. The practitioner has rotated the handle 1774 as indicated by arrow R5 to seat the tabs 1764 in the corresponding engagement slots 1283, as described above with reference to FIG. 17C. Accordingly, the main axis of the handle will be aligned with the patient's spine during insertion. The practitioner then moves the sleeve 1779 downwardly over the shaft 1769 to prevent the individual shaft sections 1763 from moving radially apart from each other. FIG. 17F illustrates a process for moving the sleeve 1779 in accordance with a particular embodiment. In this embodiment, the practitioner rotates the locking knob 1778 clockwise as indicated by arrow R6, then slides the locking knob and the sleeve 1779 toward the device 1200 as indicated by arrow T3, and then secures the locking knob 1778 in position by rotating the locking knob 1778 in a counterclockwise direction, indicated by arrow R7. FIG. 17G illustrates further details of this operation. The locking knob 1778 includes a projection that is received in a corresponding guide slot 1767, which guides the rotational and translational motion described above with reference to FIG. 17F.

Figure 17H:
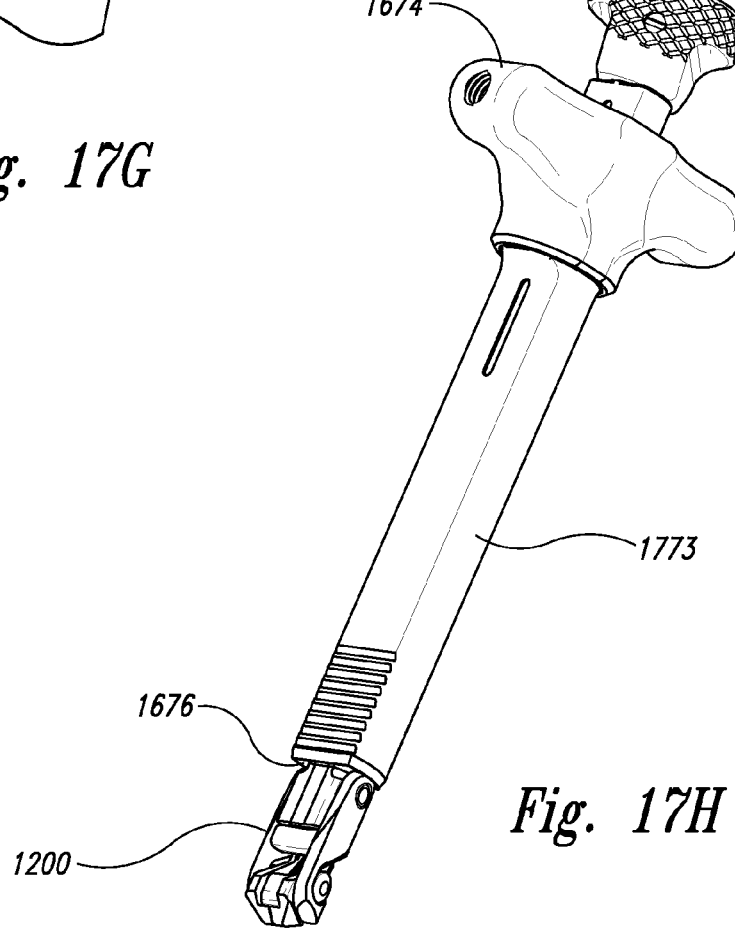
FIG. 17H illustrates the device insertion tool and device inserted into the cannula shown in FIG. 16A, in accordance with an embodiment of the disclosure.

FIG. 17H illustrates the device insertion tool 1777, with the device 1200 releasably attached to it, inserted into and through the cannula 1773, just prior to being deployed. At this point, the device 1200 is positioned between the two vertebra (not shown in FIG. 17H) positioned on each side of the cannula 1773. The practitioner then inserts a screwdriver-like actuator tool through an axially extending opening in the device insertion tool 1777, to engage with the tool slot 1247 (FIG. 17C) of the device 1200. The practitioner then deploys the spinal spacer 1210 in the manner described above with reference to FIGS. 14A-15B. To complete the procedure, the practitioner removes the actuator tool, then removes the device insertion tool 1777 (by reversing the steps described above with reference to FIGS. 17C-17G), then removes the cannula 1773, sutures the spinous ligament, and closes the skin over the insertion site.

One feature of at least some of the foregoing embodiments is that the device can include a hook member that enters the vertebral foramen to prevent or at least restrict motion of the spinal spacer device after it has been implanted. Accordingly, the likelihood that the device will be dislodged after implantation can be reduced when compared with existing devices.

Another feature of at least some of the embodiments described above is that the spinal spacer device can be inserted into the patient from a posterior direction. An advantage of this feature is that it is expected to be less invasive than procedures in which a spinal spacer is delivered laterally.

Still another feature of at least some of the foregoing embodiments is that elements of the device can be stowed as the device is implanted, and then deployed when the device reaches the implantation site. For example, the hook and/or the spinal spacer elements can be stowed during implantation and then deployed once the device is in position. An advantage of these features, alone or in combination, is that the device can be made more compact during insertion, resulting in a less invasive insertion process. At the same time, the device can include deployable features that securely and stably keep the device in position once it is implanted.

Yet another feature of at least some of the foregoing embodiments is that the actuator can be threadably engaged with the post. One advantage of this feature is that the threads between these two elements can have a relatively fine pitch, allowing the practitioner to adjust the spacing between neighboring vertebra with greater precision than is available with at least some existing devices. For example, in a particular embodiment, the practitioner can track the number of rotations he or she provides to the actuator tool, and can directly correlate this number with the deflection provided to the spinal spacer. Another expected advantage of this arrangement is that the practitioner can adjust the threaded interface between these elements in either direction, with relative ease. Accordingly, if the practitioner overdeploys the spinal spacer, he or she can partially retract the spinal spacer by simply rotating the actuator tool in the opposite direction. Still another advantage of this feature is that it is expected that the mechanical resistance of the threaded arrangement will prevent or at least resist relative motion between the post and the actuator after the device has been implanted. Accordingly, the device is less likely to retract or partially retract, or otherwise become dislodged once implanted. In particular embodiments, the actuator and post can be secured relative to each other after implantation, for example, with an adhesive or mechanical insert.

From the foregoing, it will be appreciated that specific embodiments of the disclosure have been described herein for purposes of illustration, but that various modifications may be made without deviating from the disclosure. For example, certain aspects of the spinal spacer devices and associated tools may be modified in further embodiments. Such modifications can include changing the shape of the spacing elements, and/or the hook to accommodate particular patient physiologies. In other embodiments, the post and actuator can have arrangements other than a male thread/female thread arrangement, for example, a rack and pinion arrangement. In still further embodiments, the hook can project into the vertebral foramen of the superior vertebra, and the spinal spacer can engage the inferior vertebra.

Certain aspects of the disclosure described in the context of particular embodiments may be combined or eliminated in other embodiments. For example, procedures and tools described above for inserting the device shown in FIGS. 12A-15B can be used, either as is, or modified, to insert other devices described herein. While the spinal spacer devices are illustrated as being inserted between the C3 and C4 vertebra, the devices or other embodiments of the devices can be inserted between other cervical or non-cervical vertebra. Further, while advantages associated with certain embodiments have been described in the context of those embodiments, other embodiments may also exhibit such advantages. Not all embodiments need necessarily exhibit such advantages to fall within the scope of the present disclosure. Accordingly, the disclosure can encompass other embodiments not expressly shown or described herein.

The invention claimed is:

1. A method for stabilizing a first vertebra relative to a second vertebra, comprising:
   inserting a hook member into an interspinous space between a first vertebra and a second, neighboring vertebra, with the hook member contacting the first vertebra and with a post carried by the hook member extending axially from the hook member and through an actuator;
   moving the actuator relative to the post to pivot a spinal spacer outwardly away from the post and into contact with the second vertebra; and
   continuing to move the actuator axially along the post while the hook member contacts the first vertebra and the spinal spacer contacts the second vertebra to force the first and second vertebra apart from each other.

2. The method of claim 1 wherein inserting the hook member includes inserting the hook member between the C3 and C4 vertebra.

3. The method of claim 1 wherein the first vertebra is inferior to the second vertebra, and wherein inserting the hook member includes inserting the hook member into a vertebral foramen of the first vertebra.

4. The method of claim 1 wherein the first vertebra is inferior to the second vertebra, and wherein inserting the hook member includes inserting the hook member to project in an inferior direction.

5. The method of claim 1 wherein inserting the hook member includes inserting the hook member from a posterior position.

6. The method of claim 1 wherein the hook member has multiple elements, and wherein inserting the hook member includes inserting the hook member and then moving at least one element of the hook member relative to another after the hook member is inserted.

7. The method of claim 1 wherein the actuator is threadably engaged with the post and wherein moving the actuator includes rotating the actuator to advance the actuator along the post.

8. The method of claim 1 wherein the actuator is threadably engaged with the post and wherein moving the actuator includes rotating the actuator to advance the post relative to the actuator.

9. The method of claim 1 wherein moving the actuator includes moving the actuator in opposite directions to adjust a position of the spinal spacer relative to the hook member.

10. The method of claim 1 wherein moving the spinal spacer into contact with the second vertebra includes moving the spinal spacer into contact with the spinous process of the second vertebra.

11. The method of claim 1 wherein moving the actuator includes releasably engaging the actuator with an actuator tool, moving the actuator to a desired position with the actuator tool, and releasing the actuator tool from the actuator.

12. The method of claim 1, further comprising securing the actuator in a selected position after moving the actuator to the selected position.

13. The method of claim 1 wherein moving the actuator includes moving the actuator from a position outside the interspinous space.

14. A method for stabilizing a first vertebra relative to a second vertebra, comprising:
   inserting a hook member of a device into an interspinous space between a first, inferior cervical vertebra and a second, neighboring, superior cervical vertebra, with the hook member contacting the first cervical vertebra and with a post carried by the hook member extending axially from the hook member;
   moving an actuator of the device relative to the post to simultaneously (a) pivot a spinal spacer outwardly away from the post and into contact with the second vertebra, (b) extend a portion of the hook member into a vertebral foramen of the first vertebra to at least restrict dorsal motion of the device, and (c) position spaced-apart portions of spacing elements carried by the spinal spacer on laterally opposite sides of the second vertebra to at least restrict lateral motion of the device relative to the first and second vertebra; and
   continuing to move the actuator axially while the hook member contacts the first vertebra and the spinal spacer contacts the second vertebra to force the first and second vertebra apart from each other.

15. The method of claim 14 wherein the actuator is threadably engaged with the post, and wherein moving the actuator includes rotating the actuator to axially advance the post.

16. The method of claim 15 wherein moving the actuator includes threadably adjusting a position of the actuator by rotating the actuator in a first direction and then rotating the actuator in a second direction opposite the first direction.

* * * * *